United States Patent
Saint et al.

(10) Patent No.: US 10,016,561 B2
(45) Date of Patent: Jul. 10, 2018

(54) CLINICAL VARIABLE DETERMINATION

(71) Applicant: Tandem Diabetes Care, Inc., San Diego, CA (US)

(72) Inventors: Sean Saint, San Diego, CA (US); Mike Rosinko, Anaheim, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 0 days.

(21) Appl. No.: 13/842,005

(22) Filed: Mar. 15, 2013

(65) Prior Publication Data
US 2014/0276556 A1    Sep. 18, 2014

(51) Int. Cl.
| | | |
|---|---|---|
| A61M 5/172 | (2006.01) | |
| G06F 19/00 | (2018.01) | |
| A61B 5/145 | (2006.01) | |
| A61B 5/00 | (2006.01) | |
| G16H 40/63 | (2018.01) | |

(52) U.S. Cl.
CPC ....... *A61M 5/1723* (2013.01); *A61B 5/14532* (2013.01); *A61B 5/4839* (2013.01); *A61B 5/4848* (2013.01); *G06F 19/3468* (2013.01); *G16H 40/63* (2018.01)

(58) Field of Classification Search
CPC ........ A61M 5/1723; A61M 2005/1726; A61M 5/172; A61M 5/168; A61M 2205/33; A61M 2205/3303; A61M 2230/201; A61B 5/14532; A61B 5/4839; A61B 5/4848; G06F 19/3468
USPC ............... 600/347, 365; 604/31, 65–67, 500, 604/503–504, 890.1, 892.1; 705/1–3
See application file for complete search history.

(56) References Cited

U.S. PATENT DOCUMENTS

| | | |
|---|---|---|
| 2,462,596 A | 2/1949 | Bent |
| 2,629,376 A | 2/1953 | Pierre et al. |
| 2,691,542 A | 10/1954 | Chenoweth |
| 3,059,639 A | 10/1962 | Blackman et al. |

(Continued)

FOREIGN PATENT DOCUMENTS

| | | |
|---|---|---|
| DE | 399065 | 7/1924 |
| DE | 4407005 | 3/1995 |

(Continued)

OTHER PUBLICATIONS

Application and File History for U.S. Appl. No. 13/800,595, filed Mar. 13, 2013, inventor Rosinko.

(Continued)

*Primary Examiner* — Aarti B Berdichevsky
*Assistant Examiner* — Laura Schell
(74) *Attorney, Agent, or Firm* — Patterson Thuente Pedersen, P.A.

(57) ABSTRACT

A computer implemented method of determining a clinical variables utilizing an insulin pump that includes initiating blood glucose measurements, initiating ingestion of carbohydrates and receiving input data based on the blood glucose measurements and the ingestion of carbohydrates and utilizing the data to calculate clinical variables. The invention may include presenting instructions to a patient to take various actions and to input various data. The clinical variables determined may be stored in memory and then used to calculate insulin doses and to send a signal to an insulin pump to infuse the insulin dose calculated.

6 Claims, 20 Drawing Sheets

(56) References Cited

U.S. PATENT DOCUMENTS

| | | |
|---|---|---|
| 4,393,365 A | 7/1983 | Kondo |
| 4,475,901 A | 10/1984 | Kraegen et al. |
| 5,000,664 A | 3/1991 | Lawless et al. |
| 5,050,612 A | 9/1991 | Matsumura |
| 5,122,362 A | 6/1992 | Phillips et al. |
| 5,153,827 A | 10/1992 | Coutre et al. |
| 5,181,910 A | 1/1993 | Scanlon |
| 5,219,330 A | 6/1993 | Bollish |
| 5,311,175 A | 5/1994 | Waldman |
| 5,338,157 A | 8/1994 | Blomquist |
| 5,364,346 A | 11/1994 | Schrezenmeir |
| 5,368,562 A | 11/1994 | Blomquist et al. |
| 5,376,070 A | 12/1994 | Purvis et al. |
| 5,389,078 A | 2/1995 | Zalesky et al. |
| 5,395,326 A | 3/1995 | Haber et al. |
| 5,485,408 A | 1/1996 | Blomquist |
| 5,569,186 A | 10/1996 | Lord et al. |
| 5,658,250 A | 8/1997 | Blomquist et al. |
| 5,658,252 A | 8/1997 | Johnson |
| 5,665,065 A | 9/1997 | Colman et al. |
| 5,669,877 A | 9/1997 | Blomquist |
| 5,681,285 A | 10/1997 | Ford et al. |
| 5,685,844 A | 11/1997 | Marttila |
| 5,695,473 A | 12/1997 | Olsen |
| 5,713,856 A | 2/1998 | Eggers et al. |
| 5,782,805 A | 7/1998 | Meinzer |
| 5,810,771 A | 9/1998 | Blomquist |
| 5,814,015 A | 9/1998 | Gargano et al. |
| 5,822,715 A | 10/1998 | Worthington et al. |
| 5,876,370 A | 3/1999 | Blomquist |
| 5,879,143 A | 3/1999 | Cote et al. |
| 5,885,211 A | 3/1999 | Eppstein et al. |
| 5,935,099 A | 8/1999 | Peterson et al. |
| 5,935,106 A | 8/1999 | Olsen |
| 6,023,629 A | 2/2000 | Tamada |
| 6,024,539 A | 2/2000 | Blomquist |
| 6,077,055 A | 6/2000 | Vilks |
| 6,122,536 A | 9/2000 | Sun et al. |
| 6,142,939 A | 11/2000 | Eppstein et al. |
| 6,175,752 B1 | 1/2001 | Say et al. |
| 6,233,471 B1 | 5/2001 | Berner et al. |
| 6,241,704 B1 | 6/2001 | Peterson et al. |
| 6,248,057 B1 | 6/2001 | Mavity et al. |
| 6,248,067 B1 | 6/2001 | Mavity et al. |
| 6,249,717 B1 | 6/2001 | Nicholson et al. |
| 6,272,364 B1 | 8/2001 | Kurnik |
| 6,298,254 B2 | 10/2001 | Tamada |
| 6,368,272 B1 | 4/2002 | Porumbescu |
| 6,422,057 B1 | 7/2002 | Anderson |
| 6,475,180 B2 | 11/2002 | Peterson et al. |
| 6,517,482 B1 | 2/2003 | Elden et al. |
| 6,544,212 B2 | 4/2003 | Galley et al. |
| 6,546,269 B1 | 4/2003 | Kurnik |
| 6,551,276 B1 | 4/2003 | Mann et al. |
| 6,554,798 B1 | 4/2003 | Mann et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,571,128 B2 | 5/2003 | Lebel et al. |
| 6,577,899 B2 | 6/2003 | Lebel et al. |
| 6,582,366 B1 | 6/2003 | Porumbescu |
| 6,595,919 B2 | 7/2003 | Berner et al. |
| 6,635,014 B2 | 10/2003 | Starkweather et al. |
| 6,641,533 B2 | 11/2003 | Causey, III et al. |
| 6,648,821 B2 | 11/2003 | Lebel et al. |
| 6,668,196 B1 | 12/2003 | Villegas et al. |
| 6,687,522 B2 | 2/2004 | Tamada |
| 6,694,191 B2 | 2/2004 | Starkweather et al. |
| 6,740,072 B2 | 5/2004 | Starkweather et al. |
| 6,740,075 B2 | 5/2004 | Lebel et al. |
| 6,744,350 B2 | 6/2004 | Blomquist |
| 6,771,250 B1 | 8/2004 | Oh |
| 6,773,412 B2 | 8/2004 | O'Mahony |
| 6,790,198 B1 | 9/2004 | White et al. |
| 6,809,653 B1 | 10/2004 | Mann et al. |
| 6,810,290 B2 | 10/2004 | Lebel et al. |
| 6,835,175 B1 | 12/2004 | Porumbescu |
| 6,852,104 B2 | 2/2005 | Blomquist |
| 6,872,200 B2 | 3/2005 | Mann et al. |
| 6,873,268 B2 | 3/2005 | Lebel et al. |
| 6,902,905 B2 | 6/2005 | Burson et al. |
| 6,934,220 B1 | 8/2005 | Cruitt et al. |
| 6,936,029 B2 | 8/2005 | Mann et al. |
| 6,958,705 B2 | 10/2005 | Lebel et al. |
| 6,974,437 B2 | 12/2005 | Lebel et al. |
| 6,979,326 B2 | 12/2005 | Mann et al. |
| 6,997,920 B2 | 2/2006 | Mann et al. |
| 6,998,387 B1 | 2/2006 | Goke et al. |
| 7,025,743 B2 | 4/2006 | Mann et al. |
| 7,033,338 B2 | 4/2006 | Vilks et al. |
| 7,041,082 B2 | 5/2006 | Blomquist et al. |
| 7,098,803 B2 | 8/2006 | Mann et al. |
| 7,109,878 B2 | 9/2006 | Mann et al. |
| 7,179,226 B2 | 2/2007 | Crothall et al. |
| 7,183,068 B2 | 2/2007 | Burson et al. |
| 7,204,823 B2 | 4/2007 | Estes et al. |
| 7,231,263 B2 | 6/2007 | Choi |
| 7,247,702 B2 | 7/2007 | Gardner et al. |
| 7,267,665 B2 | 9/2007 | Steil et al. |
| 7,278,983 B2 | 10/2007 | Ireland et al. |
| 7,291,107 B2 | 11/2007 | Hellwig et al. |
| 7,295,867 B2 | 11/2007 | Berner et al. |
| 7,307,245 B2 | 12/2007 | Faries et al. |
| 7,324,012 B2 | 1/2008 | Mann et al. |
| 7,341,577 B2 | 3/2008 | Gill |
| 7,404,796 B2 | 7/2008 | Ginsberg |
| 7,446,091 B2 | 11/2008 | Van Den Berghe |
| 7,471,994 B2 | 12/2008 | Ford et al. |
| 7,491,187 B2 | 2/2009 | Van Den Berghe et al. |
| 7,497,827 B2 | 3/2009 | Brister et al. |
| 7,515,060 B2 | 4/2009 | Blomquist |
| 7,547,281 B2 | 6/2009 | Hayes et al. |
| 7,553,281 B2 | 6/2009 | Hellwig et al. |
| 7,559,926 B1 | 7/2009 | Blischak |
| 7,591,801 B2 | 9/2009 | Brauker et al. |
| 7,647,237 B2 | 1/2010 | Malave et al. |
| 7,651,489 B2 | 1/2010 | Estes et al. |
| 7,674,485 B2 | 3/2010 | Bhaskaran et al. |
| 7,678,071 B2 | 3/2010 | Lebel et al. |
| 7,678,762 B2 | 3/2010 | Green et al. |
| 7,678,763 B2 | 3/2010 | Green et al. |
| 7,711,402 B2 | 5/2010 | Shults et al. |
| 7,715,893 B2 | 5/2010 | Kamath et al. |
| 7,717,903 B2 | 5/2010 | Estes et al. |
| 7,734,323 B2 | 6/2010 | Blomquist et al. |
| 7,751,907 B2 | 7/2010 | Blomquist |
| 7,766,829 B2 | 8/2010 | Sloan et al. |
| 7,768,386 B2 | 8/2010 | Hayter et al. |
| 7,768,408 B2 | 8/2010 | Reggiardo et al. |
| 7,774,145 B2 | 8/2010 | Brauker et al. |
| 7,785,313 B2 | 8/2010 | Mastrototaro |
| 7,806,886 B2 | 10/2010 | Kanderian et al. |
| 7,815,602 B2 | 10/2010 | Mann et al. |
| 7,819,843 B2 | 10/2010 | Mann et al. |
| 7,837,647 B2 | 11/2010 | Estes et al. |
| 7,869,851 B2 | 1/2011 | Hellwig et al. |
| 7,912,674 B2 | 3/2011 | Killoren et al. |
| 7,920,907 B2 | 4/2011 | McGarraugh et al. |
| 7,941,200 B2 | 5/2011 | Weinert et al. |
| 7,946,985 B2 | 5/2011 | Mastrototaro et al. |
| 7,967,773 B2 | 6/2011 | Amborn et al. |
| 7,972,296 B2 | 7/2011 | Braig et al. |
| 7,976,492 B2 | 7/2011 | Brauker et al. |
| 7,985,330 B2 | 7/2011 | Wang et al. |
| 8,005,524 B2 | 8/2011 | Brauker et al. |
| 8,012,119 B2 | 9/2011 | Estes et al. |
| 8,062,249 B2 | 11/2011 | Wilinska et al. |
| 8,066,665 B2 | 11/2011 | Rush et al. |
| 8,075,527 B2 | 12/2011 | Rush et al. |
| 8,079,983 B2 | 12/2011 | Rush et al. |
| 8,079,984 B2 | 12/2011 | Rush et al. |
| 8,083,718 B2 | 12/2011 | Rush et al. |
| 8,088,098 B2 | 1/2012 | Yodfat et al. |
| 8,093,212 B2 | 1/2012 | Gardner et al. |

(56) References Cited

U.S. PATENT DOCUMENTS

| | | |
|---|---|---|
| 8,109,921 B2 | 2/2012 | Estes et al. |
| 8,114,350 B1 | 2/2012 | Silver et al. |
| 8,119,593 B2 | 2/2012 | Richardson et al. |
| 8,127,046 B2 | 2/2012 | Grant et al. |
| 8,129,429 B2 | 3/2012 | Sporn et al. |
| 8,140,312 B2 | 3/2012 | Hayter et al. |
| 8,147,446 B2 | 4/2012 | Yodfat et al. |
| 8,152,789 B2 | 4/2012 | Starkweather et al. |
| 8,192,394 B2 | 6/2012 | Estes et al. |
| 8,204,729 B2 | 6/2012 | Sher |
| 8,206,350 B2 | 6/2012 | Mann et al. |
| 8,208,984 B2 | 6/2012 | Blomquist |
| 8,219,222 B2 | 7/2012 | Blomquist |
| 8,221,345 B2 | 7/2012 | Blomquist |
| 8,246,540 B2 | 8/2012 | Ginsberg |
| 8,250,483 B2 | 8/2012 | Blomquist |
| 8,251,906 B2 | 8/2012 | Brauker et al. |
| 8,257,259 B2 | 9/2012 | Brauker et al. |
| 8,257,300 B2 | 9/2012 | Budiman et al. |
| 8,287,495 B2 | 10/2012 | Michaud |
| 8,311,749 B2 | 11/2012 | Brauker et al. |
| 8,344,847 B2 | 1/2013 | Moberg et al. |
| 8,346,399 B2 | 1/2013 | Blomquist |
| 8,348,885 B2 | 1/2013 | Moberg et al. |
| 8,372,040 B2 | 2/2013 | Huang et al. |
| 8,444,595 B2 | 5/2013 | Brukalo et al. |
| 8,449,523 B2 | 5/2013 | Brukalo et al. |
| 8,454,510 B2 | 6/2013 | Yodfat et al. |
| 8,454,576 B2 | 6/2013 | Mastrototaro et al. |
| 8,460,231 B2 | 6/2013 | Brauker et al. |
| 8,552,880 B2 | 10/2013 | Kopp et al. |
| 8,573,027 B2 | 11/2013 | Rosinko |
| 8,650,937 B2 | 2/2014 | Brown |
| 8,657,779 B2 | 2/2014 | Blomquist |
| 8,712,748 B2 | 4/2014 | Thukral et al. |
| 8,882,701 B2 | 11/2014 | DeBelser et al. |
| 8,985,253 B2 | 3/2015 | DiPerna |
| 8,986,253 B2 | 3/2015 | DiPerna |
| 9,008,803 B2 | 4/2015 | Blomquist |
| 2001/0001144 A1 | 5/2001 | Kapp |
| 2001/0031944 A1 | 10/2001 | Peterson et al. |
| 2001/0037217 A1 | 11/2001 | Abensour et al. |
| 2001/0041831 A1 | 11/2001 | Starkweather |
| 2002/0002326 A1 | 1/2002 | Causey, III et al. |
| 2002/0065454 A1 | 5/2002 | Lebel et al. |
| 2002/0072932 A1 | 6/2002 | Swamy |
| 2002/0077852 A1 | 6/2002 | Ford et al. |
| 2002/0107476 A1 | 8/2002 | Mann et al. |
| 2002/0143580 A1 | 10/2002 | Bristol et al. |
| 2002/0183693 A1 | 12/2002 | Peterson et al. |
| 2002/0193679 A1 | 12/2002 | Malave et al. |
| 2003/0032867 A1 | 2/2003 | Crothall et al. |
| 2003/0036683 A1 | 2/2003 | Kehr et al. |
| 2003/0161744 A1 | 2/2003 | Vilks et al. |
| 2003/0050621 A1 | 3/2003 | Lebel et al. |
| 2003/0060765 A1 | 3/2003 | Campbell et al. |
| 2003/0065308 A1 | 4/2003 | Lebel et al. |
| 2003/0114836 A1 | 6/2003 | Estes et al. |
| 2003/0130616 A1 | 7/2003 | Steil et al. |
| 2003/0159945 A1 | 8/2003 | Miyazaki et al. |
| 2003/0160683 A1 | 8/2003 | Blomquist |
| 2003/0163088 A1 | 8/2003 | Blomquist |
| 2003/0163090 A1 | 8/2003 | Blomquist et al. |
| 2003/0163789 A1 | 8/2003 | Blomquist |
| 2003/0208113 A1 | 11/2003 | Mault et al. |
| 2003/0212364 A1 | 11/2003 | Mann et al. |
| 2003/0212379 A1 | 11/2003 | Bylund et al. |
| 2003/0236489 A1 | 12/2003 | Jacobson et al. |
| 2004/0015102 A1 | 1/2004 | Cummings et al. |
| 2004/0015132 A1 | 1/2004 | Brown |
| 2004/0068230 A1 | 4/2004 | Estes et al. |
| 2004/0073095 A1 | 4/2004 | Causey, III et al. |
| 2004/0115067 A1 | 6/2004 | Rush et al. |
| 2004/0152622 A1 | 8/2004 | Keith |
| 2004/0180810 A1 | 9/2004 | Pilarski |
| 2004/0193025 A1 | 9/2004 | Steil et al. |
| 2004/0193090 A1 | 9/2004 | Lebel et al. |
| 2004/0225252 A1 | 11/2004 | Gillespie, Jr. et al. |
| 2004/0254434 A1 | 12/2004 | Goodnow et al. |
| 2005/0021006 A1 | 1/2005 | Tonnies |
| 2005/0022274 A1 | 1/2005 | Campbell et al. |
| 2005/0027182 A1 | 2/2005 | Siddiqui et al. |
| 2005/0030164 A1 | 2/2005 | Blomquist |
| 2005/0065464 A1 | 3/2005 | Talbot et al. |
| 2005/0065760 A1 | 3/2005 | Murtfeldt et al. |
| 2005/0095063 A1 | 5/2005 | Fathallah et al. |
| 2005/0137530 A1 | 6/2005 | Campbell et al. |
| 2005/0143864 A1 | 6/2005 | Blomquist |
| 2005/0171513 A1 | 8/2005 | Mann et al. |
| 2005/0182358 A1 | 8/2005 | Veit et al. |
| 2005/0192557 A1 | 9/2005 | Brauker et al. |
| 2005/0197553 A1 | 9/2005 | Cooper |
| 2005/0197621 A1 | 9/2005 | Poulsen et al. |
| 2005/0228234 A1 | 10/2005 | Yang |
| 2005/0272640 A1 | 12/2005 | Doyle et al. |
| 2005/0277872 A1 | 12/2005 | Colby et al. |
| 2006/0001538 A1 | 1/2006 | Kraft |
| 2006/0001550 A1 | 1/2006 | Mann et al. |
| 2006/0014670 A1 | 1/2006 | Green et al. |
| 2006/0031094 A1 | 2/2006 | Cohen et al. |
| 2006/0047192 A1 | 3/2006 | Hellwig et al. |
| 2006/0047538 A1 | 3/2006 | Condurso et al. |
| 2006/0080059 A1 | 4/2006 | Stupp et al. |
| 2006/0085223 A1 | 4/2006 | Anderson |
| 2006/0094985 A1 | 5/2006 | Aceti et al. |
| 2006/0122577 A1 | 6/2006 | Poulsen et al. |
| 2006/0132292 A1 | 6/2006 | Blomquist |
| 2006/0137695 A1 | 6/2006 | Hellwig et al. |
| 2006/0167345 A1 | 7/2006 | Vespasiani |
| 2006/0173406 A1 | 8/2006 | Hayes et al. |
| 2006/0173444 A1 | 8/2006 | Choy et al. |
| 2006/0202859 A1 | 9/2006 | Mastrototaro et al. |
| 2006/0224109 A1 | 10/2006 | Steil et al. |
| 2006/0253097 A1 | 11/2006 | Braig et al. |
| 2006/0264895 A1 | 11/2006 | Flanders |
| 2006/0271020 A1 | 11/2006 | Huang et al. |
| 2006/0272652 A1 | 12/2006 | Stocker et al. |
| 2006/0276771 A1 | 12/2006 | Galley et al. |
| 2007/0016127 A1 | 1/2007 | Staib et al. |
| 2007/0016449 A1 | 1/2007 | Cohen et al. |
| 2007/0021733 A1 | 1/2007 | Hansen et al. |
| 2007/0033074 A1 | 2/2007 | Nitzan et al. |
| 2007/0060796 A1 | 3/2007 | Kim |
| 2007/0060871 A1 | 3/2007 | Istoc et al. |
| 2007/0060874 A1 | 3/2007 | Nesbitt et al. |
| 2007/0066956 A1 | 3/2007 | Finkel |
| 2007/0083152 A1 | 4/2007 | Williams, Jr. |
| 2007/0083335 A1 | 4/2007 | Moerman |
| 2007/0093786 A1 | 4/2007 | Goldsmith et al. |
| 2007/0100222 A1 | 5/2007 | Mastrototaro et al. |
| 2007/0106135 A1 | 5/2007 | Sloan et al. |
| 2007/0112298 A1 | 5/2007 | Mueller, Jr. et al. |
| 2007/0112299 A1 | 5/2007 | Smit et al. |
| 2007/0118405 A1 | 5/2007 | Campbell et al. |
| 2007/0124002 A1 | 5/2007 | Estes et al. |
| 2007/0149861 A1 | 6/2007 | Crothall et al. |
| 2007/0156033 A1 | 7/2007 | Causey, III et al. |
| 2007/0156457 A1 | 7/2007 | Brown |
| 2007/0173712 A1 | 7/2007 | Shah et al. |
| 2007/0203454 A1 | 8/2007 | Shermer et al. |
| 2007/0213657 A1 | 9/2007 | Jennewine et al. |
| 2007/0233051 A1 | 10/2007 | Hohl et al. |
| 2007/0251835 A1 | 11/2007 | Mehta et al. |
| 2007/0253021 A1 | 11/2007 | Mehta et al. |
| 2007/0253380 A1 | 11/2007 | Jollota et al. |
| 2007/0254593 A1 | 11/2007 | Jollota et al. |
| 2007/0255116 A1 | 11/2007 | Mehta et al. |
| 2007/0255125 A1 | 11/2007 | Moberg et al. |
| 2007/0255126 A1 | 11/2007 | Moberg et al. |
| 2007/0255250 A1 | 11/2007 | Moberg et al. |
| 2007/0258395 A1 | 11/2007 | Jollota et al. |
| 2007/0287985 A1 | 12/2007 | Estes et al. |
| 2007/0299389 A1 | 12/2007 | Halbert et al. |
| 2008/0004601 A1 | 1/2008 | Jennewine et al. |

(56) References Cited

U.S. PATENT DOCUMENTS

| | | |
|---|---|---|
| 2008/0030369 A1 | 2/2008 | Mann et al. |
| 2008/0033357 A1 | 2/2008 | Mann et al. |
| 2008/0033360 A1 | 2/2008 | Evans et al. |
| 2008/0033361 A1 | 2/2008 | Evans et al. |
| 2008/0051709 A1 | 2/2008 | Mounce et al. |
| 2008/0051714 A1 | 2/2008 | Moberg et al. |
| 2008/0051716 A1 | 2/2008 | Stutz |
| 2008/0065007 A1 | 3/2008 | Peterson |
| 2008/0065016 A1 | 3/2008 | Peterson |
| 2008/0071209 A1 | 3/2008 | Moubayed |
| 2008/0071210 A1 | 3/2008 | Moubayed |
| 2008/0071217 A1 | 3/2008 | Moubayed |
| 2008/0071251 A1 | 3/2008 | Moubayed |
| 2008/0071580 A1 | 3/2008 | Marcus et al. |
| 2008/0076969 A1 | 3/2008 | Kraft et al. |
| 2008/0097289 A1 | 4/2008 | Steil et al. |
| 2008/0106431 A1 | 5/2008 | Blomquist |
| 2008/0114299 A1 | 5/2008 | Damgaard-Sorensen et al. |
| 2008/0132844 A1 | 6/2008 | Peterson |
| 2008/0139907 A1 | 6/2008 | Rao et al. |
| 2008/0147004 A1 | 6/2008 | Mann et al. |
| 2008/0147050 A1 | 6/2008 | Mann et al. |
| 2008/0154513 A1 | 6/2008 | Kovatchev et al. |
| 2008/0171697 A1 | 7/2008 | Jacotot et al. |
| 2008/0171967 A1 | 7/2008 | Blomquist et al. |
| 2008/0172026 A1 | 7/2008 | Blomquist |
| 2008/0172027 A1 | 7/2008 | Blomquist |
| 2008/0172028 A1 | 7/2008 | Blomquist |
| 2008/0172029 A1 | 7/2008 | Blomquist |
| 2008/0172030 A1 | 7/2008 | Blomquist |
| 2008/0172031 A1 | 7/2008 | Blomquist |
| 2008/0177165 A1* | 7/2008 | Blomquist et al. .......... 600/365 |
| 2008/0206799 A1 | 8/2008 | Blomquist |
| 2008/0228056 A1 | 9/2008 | Blomquist et al. |
| 2008/0249470 A1 | 10/2008 | Malave et al. |
| 2008/0255438 A1 | 10/2008 | Saidara et al. |
| 2008/0255517 A1 | 10/2008 | Nair et al. |
| 2008/0269585 A1 | 10/2008 | Gingsberg |
| 2008/0269714 A1 | 10/2008 | Mastrototaro et al. |
| 2008/0269723 A1 | 10/2008 | Mastrototaro et al. |
| 2008/0287922 A1 | 11/2008 | Panduro |
| 2008/0288115 A1 | 11/2008 | Rusnak et al. |
| 2008/0294024 A1 | 11/2008 | Cosentino et al. |
| 2008/0294142 A1 | 11/2008 | Patel et al. |
| 2008/0294294 A1 | 11/2008 | Blomquist |
| 2008/0300534 A1 | 12/2008 | Blomquist |
| 2008/0300572 A1 | 12/2008 | Rankers et al. |
| 2008/0312585 A1 | 12/2008 | Brukalo et al. |
| 2009/0018779 A1 | 1/2009 | Cohen et al. |
| 2009/0030733 A1 | 1/2009 | Cohen et al. |
| 2009/0069745 A1 | 3/2009 | Estes et al. |
| 2009/0069787 A1 | 3/2009 | Estes et al. |
| 2009/0088731 A1 | 4/2009 | Campbell et al. |
| 2009/0093756 A1 | 4/2009 | Minaie |
| 2009/0105636 A1 | 4/2009 | Hayter |
| 2009/0105646 A1 | 4/2009 | Hendrixson et al. |
| 2009/0131860 A1 | 5/2009 | Nielsen |
| 2009/0150186 A1 | 6/2009 | Cohen et al. |
| 2009/0163855 A1 | 6/2009 | Shin et al. |
| 2009/0171269 A1 | 7/2009 | Jennewine et al. |
| 2009/0177142 A1 | 7/2009 | Blomquist et al. |
| 2009/0177147 A1 | 7/2009 | Blomquist et al. |
| 2009/0177154 A1 | 7/2009 | Blomquist |
| 2009/0177180 A1 | 7/2009 | Rubalcaba |
| 2009/0192366 A1 | 7/2009 | Mensinger et al. |
| 2009/0192724 A1 | 7/2009 | Bauker et al. |
| 2009/0192745 A1 | 7/2009 | Kamath et al. |
| 2009/0212966 A1 | 8/2009 | Panduro |
| 2009/0216100 A1 | 8/2009 | Ebner et al. |
| 2009/0247931 A1 | 10/2009 | Damgaard-Sorensen |
| 2009/0247982 A1 | 10/2009 | Krulevitch et al. |
| 2009/0281393 A1 | 11/2009 | Smith |
| 2010/0008795 A1 | 1/2010 | DiPerna |
| 2010/0030045 A1 | 2/2010 | Gottlieb et al. |
| 2010/0030387 A1 | 2/2010 | Sen |
| 2010/0057043 A1 | 3/2010 | Kovatchev et al. |
| 2010/0069730 A1 | 3/2010 | Bergstrom et al. |
| 2010/0081993 A1 | 4/2010 | O'Connor |
| 2010/0094110 A1 | 4/2010 | Heller et al. |
| 2010/0095229 A1 | 4/2010 | Dixon et al. |
| 2010/0105999 A1 | 4/2010 | Dixon et al. |
| 2010/0121169 A1 | 5/2010 | Petisce et al. |
| 2010/0121170 A1 | 5/2010 | Rule |
| 2010/0125241 A1 | 5/2010 | Prud et al. |
| 2010/0130933 A1 | 5/2010 | Holland et al. |
| 2010/0138197 A1 | 6/2010 | Sher |
| 2010/0145276 A1 | 6/2010 | Yodfat et al. |
| 2010/0174266 A1 | 7/2010 | Estes |
| 2010/0174553 A1 | 7/2010 | Kaufman et al. |
| 2010/0179402 A1 | 7/2010 | Goode et al. |
| 2010/0185142 A1 | 7/2010 | Kamen et al. |
| 2010/0185175 A1 | 7/2010 | Kamen et al. |
| 2010/0198142 A1 | 8/2010 | Sloan et al. |
| 2010/0222765 A1 | 9/2010 | Blomquist et al. |
| 2010/0228186 A1 | 9/2010 | Estes et al. |
| 2010/0249530 A1 | 9/2010 | Rankers et al. |
| 2010/0262117 A1 | 10/2010 | Magni et al. |
| 2010/0262434 A1* | 10/2010 | Shaya .................. A61B 5/7475 705/3 |
| 2010/0274592 A1 | 10/2010 | Nitzan et al. |
| 2010/0274751 A1 | 10/2010 | Blomquist |
| 2010/0280329 A1 | 11/2010 | Randløv et al. |
| 2010/0286601 A1 | 11/2010 | Yodfat et al. |
| 2010/0292634 A1 | 11/2010 | Kircher, Jr. et al. |
| 2010/0298685 A1* | 11/2010 | Hayter ............... A61B 5/14532 600/365 |
| 2010/0312085 A1 | 12/2010 | Andrews et al. |
| 2010/0324382 A1 | 12/2010 | Cantwell et al. |
| 2010/0324398 A1 | 12/2010 | Tzyy-Ping |
| 2010/0331651 A1 | 12/2010 | Groll |
| 2011/0033833 A1 | 2/2011 | Blomquist et al. |
| 2011/0040247 A1 | 2/2011 | Mandro et al. |
| 2011/0040251 A1 | 2/2011 | Blomquist |
| 2011/0047499 A1 | 2/2011 | Mandro et al. |
| 2011/0053121 A1 | 3/2011 | Heaton |
| 2011/0054390 A1 | 3/2011 | Searle et al. |
| 2011/0054391 A1 | 3/2011 | Ward et al. |
| 2011/0056264 A1 | 3/2011 | Kaplan |
| 2011/0071765 A1 | 3/2011 | Yodfat et al. |
| 2011/0092788 A1 | 4/2011 | Long et al. |
| 2011/0098548 A1 | 4/2011 | Budiman et al. |
| 2011/0098637 A1 | 4/2011 | Hill |
| 2011/0098638 A1 | 4/2011 | Chawla et al. |
| 2011/0098674 A1 | 4/2011 | Vicente et al. |
| 2011/0106011 A1 | 5/2011 | Cinar et al. |
| 2011/0106050 A1 | 5/2011 | Yodfat et al. |
| 2011/0112505 A1 | 5/2011 | Starkweather et al. |
| 2011/0112506 A1 | 5/2011 | Starkweather et al. |
| 2011/0118578 A1 | 5/2011 | Timmerman |
| 2011/0118699 A1 | 5/2011 | Yodfat et al. |
| 2011/0124996 A1 | 5/2011 | Reinke et al. |
| 2011/0130746 A1 | 6/2011 | Budiman |
| 2011/0137239 A1 | 6/2011 | Debelser et al. |
| 2011/0144586 A1 | 6/2011 | Michaud et al. |
| 2011/0152770 A1 | 6/2011 | Diperna et al. |
| 2011/0160695 A1 | 6/2011 | Sigrist et al. |
| 2011/0166875 A1 | 7/2011 | Hayter et al. |
| 2011/0178717 A1 | 7/2011 | Goodnow et al. |
| 2011/0184342 A1 | 7/2011 | Pesach et al. |
| 2011/0196213 A1 | 8/2011 | Thukral et al. |
| 2011/0205065 A1 | 8/2011 | Strachan et al. |
| 2011/0257895 A1 | 10/2011 | Brauker et al. |
| 2011/0266999 A1 | 11/2011 | Yodfat et al. |
| 2012/0029941 A1 | 2/2012 | Malave et al. |
| 2012/0030610 A1 | 2/2012 | DiPerna et al. |
| 2012/0041415 A1 | 2/2012 | Estes et al. |
| 2012/0053522 A1 | 3/2012 | Yodfat et al. |
| 2012/0059353 A1 | 3/2012 | Kovatchev et al. |
| 2012/0059673 A1 | 3/2012 | Cohen et al. |
| 2012/0095315 A1 | 4/2012 | Tenbarge et al. |
| 2012/0123230 A1 | 5/2012 | Brown et al. |
| 2012/0163481 A1 | 6/2012 | Ebner et al. |
| 2012/0226124 A1 | 9/2012 | Blomquist |
| 2012/0232484 A1 | 9/2012 | Blomquist |

(56) References Cited

U.S. PATENT DOCUMENTS

| | | |
|---|---|---|
| 2012/0232485 A1 | 9/2012 | Blomquist |
| 2012/0232520 A1 | 9/2012 | Sloan et al. |
| 2012/0232521 A1 | 9/2012 | Blomquist |
| 2012/0238852 A1 | 9/2012 | Brauker et al. |
| 2012/0238854 A1 | 9/2012 | Blomquist et al. |
| 2012/0239362 A1 | 9/2012 | Blomquist |
| 2012/0245524 A1 | 9/2012 | Estes et al. |
| 2012/0265722 A1 | 10/2012 | Blomquist |
| 2012/0296269 A1 | 11/2012 | Blomquist |
| 2012/0330227 A1 | 12/2012 | Budiman et al. |
| 2013/0053816 A1 | 2/2013 | DiPerna |
| 2013/0131630 A1 | 5/2013 | Blomquist |
| 2013/0324928 A1 | 12/2013 | Kruse |
| 2013/0331790 A1 | 12/2013 | Brown et al. |
| 2014/0012511 A1 | 1/2014 | Mensinger et al. |
| 2014/0066890 A1 | 3/2014 | Sloan et al. |
| 2014/0074059 A1 | 3/2014 | Howell et al. |
| 2014/0137641 A1 | 5/2014 | Brown |
| 2014/0171772 A1 | 6/2014 | Blomquist |
| 2014/0273042 A1 | 9/2014 | Saint |
| 2014/0275419 A1 | 9/2014 | Ward et al. |
| 2014/0276419 A1 | 9/2014 | Rosinko et al. |
| 2014/0276420 A1 | 9/2014 | Rosinko |
| 2014/0276531 A1 | 9/2014 | Walsh |
| 2014/0276553 A1 | 9/2014 | Rosinko |
| 2014/0276556 A1 | 9/2014 | Saint et al. |
| 2014/0276574 A1 | 9/2014 | Saint |
| 2014/0350371 A1 | 11/2014 | Blomquist et al. |
| 2014/0378898 A1 | 12/2014 | Rosinko |
| 2015/0073337 A1 | 3/2015 | Saint et al. |
| 2015/0182693 A1 | 7/2015 | Rosinko |
| 2015/0182695 A1 | 7/2015 | Rosinko |
| 2015/0217044 A1 | 8/2015 | Blomquist |
| 2015/0314062 A1 | 11/2015 | Blomquist et al. |
| 2016/0030669 A1 | 2/2016 | Harris et al. |
| 2016/0082188 A1 | 3/2016 | Blomquist et al. |
| 2016/0199571 A1 | 7/2016 | Rosinko et al. |
| 2016/0228041 A1 | 8/2016 | Heller et al. |

FOREIGN PATENT DOCUMENTS

| | | |
|---|---|---|
| DE | 19819407 | 11/1999 |
| DE | 10121317 | 11/2002 |
| DE | 10352456 | 7/2005 |
| EP | 1102194 | 5/2001 |
| EP | 1571582 | 9/2005 |
| JP | JP2006034323 | 2/2006 |
| WO | WO0045696 | 8/2000 |
| WO | WO0074753 | 12/2000 |
| WO | WO0152727 | 7/2001 |
| WO | WO02062212 | 8/2002 |
| WO | WO03082091 | 10/2003 |
| WO | WO2005046559 | 5/2005 |
| WO | WO06061169 | 6/2006 |
| WO | WO2006127841 | 11/2006 |
| WO | WO2007000425 | 1/2007 |
| WO | WO2007056592 | 5/2007 |
| WO | WO2007089537 | 8/2007 |
| WO | WO07149533 | 12/2007 |
| WO | WO2008048556 | 4/2008 |
| WO | WO2008048582 | 4/2008 |
| WO | WO2008048583 | 4/2008 |
| WO | WO2008048584 | 4/2008 |
| WO | WO2008048585 | 4/2008 |
| WO | WO2008048586 | 4/2008 |
| WO | WO2008048587 | 4/2008 |
| WO | WO2008091320 | 7/2008 |
| WO | WO2008112078 | 9/2008 |
| WO | WO2008153689 | 12/2008 |
| WO | WO2008153819 | 12/2008 |
| WO | WO2009016636 | 2/2009 |
| WO | WO 2009/032400 A1 | 3/2009 |
| WO | WO2009035759 A1 | 3/2009 |
| WO | WO09089028 | 7/2009 |
| WO | WO2009088983 | 7/2009 |
| WO | WO2009089029 | 7/2009 |
| WO | WO2011068648 | 6/2011 |
| WO | WO 2013/016363 A1 | 1/2013 |
| WO | WO2013184896 A1 | 12/2013 |

OTHER PUBLICATIONS

Application and File History for U.S. Appl. No. 14/962,635, filed Dec. 8, 2015, inventors Blomquist et al.

Application and File History for U.S. Appl. No. 11/685,617, filed Mar. 13, 2007, inventors Blomquist et al.

International Search Report and Written Opinion for International Application No. PCT/US200900034 dated May 27, 2009.

Walsh, "Diabetes Technology Concept 1: Super Bolus" Online. http://www.diabetesnet.com/diabetes_technology/super_bolus.php> Sep. 17, 2007. (3 pages).

International Preliminary Report and Written Opinion for International Application No. PCT/US2010/056233 date of issuance of this report is Jun. 5, 2012.

PCT Search Report dated Aug. 31, 2011 for PCT Application No. PCT/US2010/056233 filed Nov. 10, 2010.

International Search Report and Written Opinion for International Application No. PCT/US2007/024423 dated May 19, 2008.

International Search Report and Written Opinion for International Application No. PCT/US2009/000106 dated May 13, 2009.

Plougmann et al, "DiasNet—a diabetes advisory system for communication and education via the internet", International Journal of Medical Informatics, vol. 26, pp. 319-330 (2001).

Wilinska et al., "Insulin Kinetics in Type-1 Diabetes: Continuous and Bolus Delivery of Reapid Acting Insulin>" IEEE Transactions on Bopmedical Engineering vol. 52. No. 1, pp. 3-12. Jan. 2005.

Bott et al, "Impact of Smoking on the Metabolic Action of Subcutaneous Regular Insulin in Type 2 Diabetic Patients" Horm. Metab. Res., vol. 37, pp. 445-449 (2005).

Puckett et al., Am. J. Physiol. vol. 269, p. E1115-E1124, 1995 "A Model for Multiple Subcutaneous Insulin Injections Developed from Individual Diabetic Patient Data".

Wach et al., Med & Biol. Eng & comput., vol. 33, p. 18-23, 1995. "Numerical Approximation of Mathematical Model for Absorption of Subcutaneously Injected Insulin".

Lehmann et al., Artificial intelligence in Medicine, vol. 6, p. 137-160,1994. Combining rule-based reasoning and mathematical modeling in diabetes care.

Chase et al., The Use of Insulin Pumps With Meal Bolus Alarms in Children With Type 1 Diabetes to Improve Glycemic Control, Diabetes Carem vol. 29, No. 5. May 2006. 1012-1015.

International Search Report for International Application No. PCT/US2007/022050 dated Mar. 7, 2008.

International Search Report for International Application No. PCT/US09/00107 dated May 4, 2009.

International Search Report for International Application No. PCT/US2009/000034 dated May 27, 2009.

International Search Report for International Application No. PCT/US2009/000106 dated May 13, 2009.

International Search Report from International Application No. PCT/US2007/024423 dated May 19, 2008.

Stapel, Elizabeth, "Converting Between Decimals, Fractions, and Percents", Purplemath. 2006. http://www.purplemath.com/modules/percents2.htm.

Written Opinion for International Application No. PCT/US2009/000034 dated May 27, 2009.

Written Opinion for International Application No. PCT/US2009/000106 dated May 13, 2009.

Written Opinion for International Application No. PCT/US2007/024423 dated May 19, 2008.

International Search Report for International Application No. PCT/US2007/022046 dated Mar. 7, 2008.

Written Opinion for International Application No. PCT/US2007/022046 dated Mar. 7, 2008.

Trajanoski et al., Pharmacokinetic Model for the Absorption of Subcutaneoutsly Injected Soluble Insulin and Monomeric Insulin Analogues. Biomedizinische Technik,. vol. 38 No. 9. Sep. 1, 1993.

(56) References Cited

OTHER PUBLICATIONS

Hildebrandt, Subcutaneous Absorption of Insulin in Insulin-Dependent Diavetic patients. Influence of Species Physico-Chemical properties of Insulin and Physiological factors. Danish Medical Bulletin. Aug. 1991.
Written Opinion for International Application No. PCT/US2007/022004 dated Oct. 9, 2008.
International Search Report for International Application No. PCT/US2007/022004 dated Oct. 9, 2008.
Written Opinion for International Application No. PCT/US2007/022047 dated Mar. 7, 2008.
International Search Report for International Application No. PCT/US2007/022047 dated Mar. 7, 2008.
Written Opinion for International Application No. PCT/US2007/022048 dated Mar. 7, 2008.
International Search Report for International Application No. PCT/US2007/022048 dated Mar. 7, 2008.
Written Opinion for International Application No. PCT/US2007/022049 dated Mar. 7, 2008.
International Search Report for International Application No. PCT/US2007/022049 dated Mar. 7, 2008.
International Search Report for International Application No. PCT/US2007/022051 dated Mar. 7, 2008.
Written Opinion for International Application No. PCT/US2007/022051 dated Mar. 7, 2008.
International Search Report for International Application No. PCT/US2007/022052 dated May 11, 2007.
Written Opinion for International Application No. PCT/US2007/022052 dated May 11, 2007.
European Office Action from European Application No. 07852760.3 dated Aug. 11, 2010.
Written Opinion and International Search Report for International Application No. PCT/US2008/002536 dated Sep. 4, 2008.
Application and File History for U.S. Appl. No. 14/455,508, filed Aug. 8, 2014, inventors Blomquist et al.
European Search Report for European Application No. 15168432 dated completed Sep. 1, 2015 and dated Sep. 8, 2015.
Application and File History for U.S. Appl. No. 13/800,453, filed Mar. 13, 2013, inventors Rosinko et al.
Application and File History for U.S. Appl. No. 14/187,414, filed Feb. 24, 2014, inventor Blomquist.
International Search Report and Written Opinion for International Application No. PCT/US2014/021109 dated Jun. 5, 2014.
Application and File History for U.S. Appl. No. 14/813,699, filed Jul. 30, 2015, inventors Harris et al.
International Search Report and Written Opinion for International Application No. PCT/US2015/042881 dated Nov. 11, 2015.
Application and File History for U.S. Appl. No. 11/626,653, filed Jan. 24, 2007, inventors Blomquist et al.
International Search Report and Written Opinion for International Application No. PCT/US2007/024424 dated Mar. 6, 2009.
Walsh et al., "Select & Test Your Correction Factor" Pumping Insulin, Fourth Edition, Chapter 13 (2006), 29 pages.
Application and File History for U.S. Appl. No. 12/720,306, filed Mar. 9, 2010, inventors Blomquist et al.
Wikipedia's definition for "basal rate", 1 page. Printed from Wikipedia.com on Jun. 12, 2009.
Compare Insulin Pump for Diabetes. 4 pages. Printed www.diabetesnet.com on Jun. 18, 2009.
Walsh et al., "Pumping Insulin: Everything You Need for Success on a Smart Insulin Pump", Torrey Pines Press (2006).
Deltec Cozmo. Personalized Insulin Pump, Starting Guide. http://web.archive.org/web/20041207133233/http://www,cozmore.com/Library/upload/starting_guide_032004.pdf. Dec. 7, 2004.
Written Opinion and International Search Report for international Application Serial No. PCT/US2008/006449 dated Oct. 10, 2008.
Written Opinion and International Search Report for International Application Serial No. PCT/US2008/006801 dated Oct. 30, 2008.
Application and File History for U.S. Appl. No. 11/753,420, filed May 24, 2007, inventors Blomquist.
Application and File History for U.S. Appl. No. 12/774,991 filed May 6, 2010, inventor Blomquist.
Application and File History for U.S. Appl. No. 13/530,404, filed Jun. 22, 2012, inventor Blomquist.
IPRP and Written Opinion for International Application No. PCT/US2010/056226 dated Jun. 14, 2012.
Canadian Office Action for Canadian Application No. 2,782,673 dated Sep. 10, 2013.
European Office Action for European Application No. 08779626.4 dated May 25, 2010.
European Office Action for European Application No. 08767734.6 dated Apr. 7, 2010. 6 pages.
Application and File History for U.S. Appl. No. 12/631,076, filed Dec. 4, 2009, inventor DeBelser et al.
Japanese Office Action for Japanese Application No. 2012542037 dated Sep. 2, 2014.
Chinese Office Action for Chinese Application No. 201080063326.9 dated Jan. 27, 2014.

\* cited by examiner

CLINICAL VARIABLE DETERMINATION

FIELD OF THE INVENTION

The invention relates to determining clinical variables that are utilized in the operation of an insulin pump. Such clinical variables may include insulin sensitivity factor and the carbohydrate factor, also known as the insulin to carbohydrate ratio. The invention also relates to systems and methods for automating the determination of these clinical variables.

BACKGROUND OF THE INVENTION

The control of insulin pump therapy benefits greatly from knowing certain clinical variables including the insulin sensitivity factor and the carbohydrate factor, also known as carb factor or the insulin to carbohydrate ratio. Typically, these factors are determined by a manual method of administering insulin or carbohydrates and observing the effect of this administration on blood glucose level.

Calculation of insulin sensitivity factor is based on all of the units of insulin that a person takes in one day. Insulin sensitivity factor is also sometimes referred to as correction factor or correction bolus and is based on the drop in blood glucose level caused by one unit of insulin in units of milligrams per deciliter (mg/dL). Patients who are using insulin find that there are times when they need to make insulin adjustments in order to maintain blood glucose within target levels. In some cases, patients need to add more insulin at meal times to correct for high blood glucose. At other times, it may be necessary to correct a high blood glucose that is not associated with a meal. To utilize the insulin sensitivity factor to apply a corrective dose of insulin, it is necessary to know how many milligrams per deciliter one unit of insulin lowers the blood glucose. This value may vary with the individual patient and may also vary throughout the day or during times of illness. Generally, the goal is to apply a correction bolus that returns the blood glucose level to within thirty milligrams per deciliter of the target blood glucose level within three hours after the dose is given.

One method of calculating the insulin sensitivity factor is to take a three-day average of the total amount of insulin taken per day. This may be done by adding the basal daily total units of insulin taken in a given day to the bolus daily total units of insulin taken in that day to arrive at a total insulin value for that day. The insulin sensitivity factor is then determined by dividing a constant by the total daily insulin intake. Depending upon the type of insulin used, the constant varies. For some types of insulin the constant is considered to be 1,800; for other types of insulin the constant is considered to be 1,700; for yet other types of insulin, the constant is considered to be 1,500. In general, the 1500 sensitivity constant, sometimes referred to as the "1500 rule", is used to estimate the blood glucose level drop, in milligrams per deciliter, for every unit of regular insulin taken. The 1800 sensitivity constant, sometimes referred to as the "1800 rule", is used to estimate the blood glucose level drop, in milligrams per deciliter, for every unit of rapid-acting insulin taken. For example, if a patient has utilized thirty units total insulin daily and a correction constant of 1500 is used, 1500 divided by thirty equals fifty. This means that one unit of insulin would typically lower blood glucose for that patient by approximately 50 milligrams per deciliter (mg/dL).

The insulin sensitivity factor or correction factor is then used to calculate an insulin correction bolus dose. The correction bolus dose is calculated by subtracting from the current blood glucose level the target blood glucose and then dividing that difference by the insulin sensitivity factor. For example, if a patient has a current blood glucose of 200 milligrams per deciliter, and a target blood glucose of 100 milligrams per deciliter, 200 less 100 equals 100. 100 divided by the correction factor of 50 indicates that 2.0 units of insulin should be given for a correction dose.

The carbohydrate factor, also known as insulin to carbohydrate ratio or insulin to carb ratio, helps determine how much insulin should be taken to provide for proper metabolism of carbohydrates that would be eaten at a meal or in a snack. Carb ratios are calculated on a variable basis. For example, some patients might take 1.5 units of insulin for every carbohydrate choice, while others might take 1 unit of insulin for every 10 grams of carbohydrate that is expected to be eaten. Insulin-to-carb ratios vary from person to person and insulin to-carb-ratio may change over the course of treatment for some patients. Insulin to carb ratio may even vary depending upon the time of day.

Carb factors are commonly calculated using the "500 rule" (which is also sometimes known as the "450 rule" when using regular, non-fast acting insulin). Once the carb factor is known, the number of grams of carbohydrates in food that is to be eaten can be divided by the carb factor to determine how many units of bolus insulin is needed to cover metabolism of the carbohydrates that are to be eaten. This option provides patients flexibility in their food choices because the number of carbohydrates being ingested can be compensated for with a matching dose of insulin. According to the 500 or the 450 rule, an estimate of the number of grams of carbohydrates metabolized per unit of fast-acting insulin is determined. A constant of 450 is used for calculation with regular insulin. For example, when utilizing rapid-acting insulin, the constant of 500 is divided by the total daily dose of insulin to determine the grams of carbohydrates that are covered by one unit of rapid-acting insulin. The total daily insulin, sometimes abbreviated TDD, includes all fast-acting insulin taken before meals plus all long acting insulin used in a day. Correction doses of rapid-acting insulin taken to correct high blood glucose readings during the day should also be factored into the daily dosage.

The 500 rule is most accurate for those whose bodies make no insulin of their own and who receive 50 to 60 percent of their total daily dosage as basal insulin. For patients utilizing an insulin pump, the determined values used are then manually entered into the insulin pump where they are used to control insulin dosage. Examples of such pumps and various features that can be associated with such pumps include those disclosed in U.S. patent application Ser. No. 13/557,163, U.S. patent application Ser. No. 12/714,299, U.S. patent application Ser. No. 12/538,018, U.S. Provisional Patent Application No. 61/655,883, U.S. Provisional Patent Application No. 61/656,967 and U.S. Pat. No. 8,287,495, each of which is incorporated herein by reference.

However, none of the above estimation techniques for insulin sensitivity factor or carbohydrate factor is as accurate as would be ideal. Further, many patients are well-known to be non-compliant with medication regimens, particularly when the regimen becomes more complex or burdensome. Accordingly, there is still room for improvement in these areas.

SUMMARY OF THE INVENTION

The present invention relates to automating or partially automating the determination of values for insulin sensitivity factor, carbohydrate factor and insulin action time in the context of "smart" insulin pumps; particularly in some embodiments, a smart insulin pump having a larger display. According to the invention, the pump or another electronic device queries and instructs the patient through the process of determining clinical variables such as, for example, the insulin sensitivity factor or the carbohydrate factor (also known as the carb ratio). Further, the invention contemplates the incorporation of continuous glucose monitoring (CGM) into the determination of the insulin sensitivity factor or the carbohydrate factor by taking advantage of the tracking and trending strengths of CGM.

According to one embodiment of the invention, the controller of the insulin pump provides directions for what the patient should do, including either prompting the patient to take blood glucose measurements (e.g., by obtaining a blood sample via a finger stick and testing the blood glucose level directly with a blood glucose meter as is commonly done) or taking advantage of the monitoring estimates of a patient's blood glucose level through a continuous glucose monitoring system. A CGM system provides a substantially continuous estimated blood glucose level through a transcutaneous sensor that measures analytes, such as glucose, in the patient's interstitial fluid rather than their blood. Examples of CGMs include the Seven®, Seven® PLUS, and G4™ Platinum monitoring systems sold by Dexcom®, Inc. of San Diego, Calif. CGM systems typically consist of a transcutaneously-placed sensor, a transmitter, and a monitor (either a stand-alone monitor or one built into an insulin pump). Such systems and definitions of related terms are described in greater detail in, e.g.: U.S. Pat. Nos. 8,311,749; 7,711,402; and 7,497,827; each of which is hereby incorporated by reference in its entirety. A CGM system enables a patient or caregiver to insert a single sensor probe under the skin for multiple days, such as for a week. Thus, the patient is only required to perform a single moderately invasive action with a single entry point in the subdermal layer on, e.g., a weekly basis. The system estimates the level of blood glucose periodically and sends that information to a monitor that is carried by the patient. Because the CGM estimates blood glucose levels from analyzing interstitial plasma or fluid, rather than from analyzing blood as is done with blood glucose meters, however, CGMs generally are not as well-suited for accurate blood glucose monitoring. Accordingly, CGMs are most often used for identifying trends in blood glucose levels over time and for providing estimates thereof. Typically, after a monitoring period, during which the patient or caregiver can monitor estimated blood glucose levels in real-time, the sensor is removed and information stored in the continuous glucose monitoring system may be, e.g., downloaded into a computer for analysis.

According to one example embodiment, the invention asks the user to ingest a certain amount of carbohydrates and prompts them to take blood glucose measurements before and at a certain time after the ingestion of carbohydrates. The prompts may be directed to the patient who takes the measurement and inputs it. The prompts may be initiated based on input from a CGM system.

As mentioned, the CGM system is particularly useful for trending and tracking of estimated blood glucose levels while being less useful for identifying precise numerical values for actual blood glucose levels. Thus, the CGM can be incorporated to identify when blood glucose is rising, falling or is flat for a period of time. According to the invention, these factors can be used to identify when to prompt a patient to take a blood glucose measurement and to input the findings of the measurement into the infusion pump controller to gather data to determine insulin sensitivity factor or carb factor.

Based on this information, the carb ratio may then be determined automatically by the controller. The carbohydrate ratio can then be automatically set into the pump for use in further applications of insulin based on ingestion of carbohydrates.

According to another embodiment, the invention includes determining insulin action time. After a bolus of insulin is infused, blood glucose level will decrease. This reduction is observable with CGM. Accordingly this method is well suited to be performed along with the insulin sensitivity factor determination discussed herein. After a bolus of insulin is infused the time for a selected reduction in blood glucose level to be achieved is recorded. This determines the insulin action time.

A method of determining insulin action time, according to an embodiment of the invention, includes infusing a bolus of insulin; waiting a minimum period of time; receiving an input from the CGM that the blood glucose level has reached a level or stable state and identifying the insulin action time by noting the time between infusion of insulin and the achieving of the level or stable state. Alternately, the fall in blood glucose level according to the CGM can be extrapolated to an inflection point from when the blood glucose level decline is most rapid. Alternately, the fall in blood glucose level according to the CGM can be extrapolated from a time when substantially all of the blood glucose decrease has occurred. For example, extrapolation can be based on a point wherein approximately seventy five percent of the blood glucose decrease has occurred. The time between infusion of the insulin and the inflection point can be taken as the insulin action time. The fall in blood glucose level can also be extrapolated from a time when significantly all of the blood glucose decrease has occurred, such as, for example, after 75% of the decrease has occurred.

DETAILED DESCRIPTION

Provided herein are systems, devices and methods for accurately determining clinical variables in an infusion pump and particularly in an insulin infusion pump. Examples of such pumps and various features that can be associated with such pumps include those disclosed in U.S. patent application Ser. No. 13/557,163, U.S. patent application Ser. No. 12/714,299, U.S. patent application Ser. No. 12/538,018, U.S. Provisional Patent Application No. 61/655,883, U.S. Provisional Patent Application No. 61/656,967 and U.S. Pat. No. 8,287,495, each of which is incorporated herein by reference.

Some embodiments may include advances in the internal components, the control circuitry, and improvements in a user interface of the systems and devices. The advances may allow for a safer and more accurate delivery of medicament to a patient than is currently attainable today from other devices, systems, and methods. Although embodiments described herein may be discussed in the context of the controlled delivery of insulin, delivery of other medicaments as well as other applications are also contemplated. Device and method embodiments discussed herein may be used for pain medication, chemotherapy, iron chelation, immunoglobulin treatment, dextrose or saline IV delivery, or any other suitable indication or application. Non-medical applications are also contemplated.

Figure 1A:
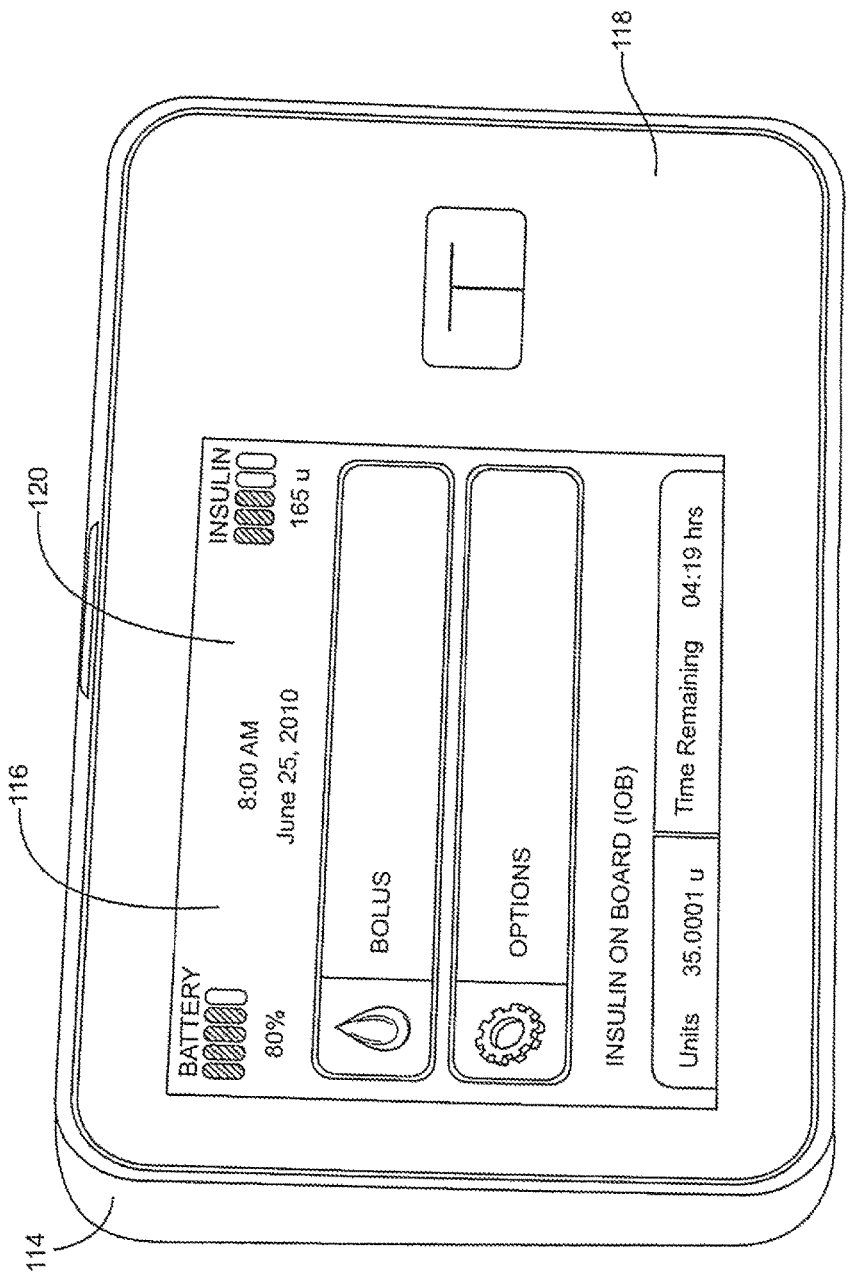
FIG. 1A is a front perspective view of an embodiment of a portable infusion pump system.
Figure 1B:
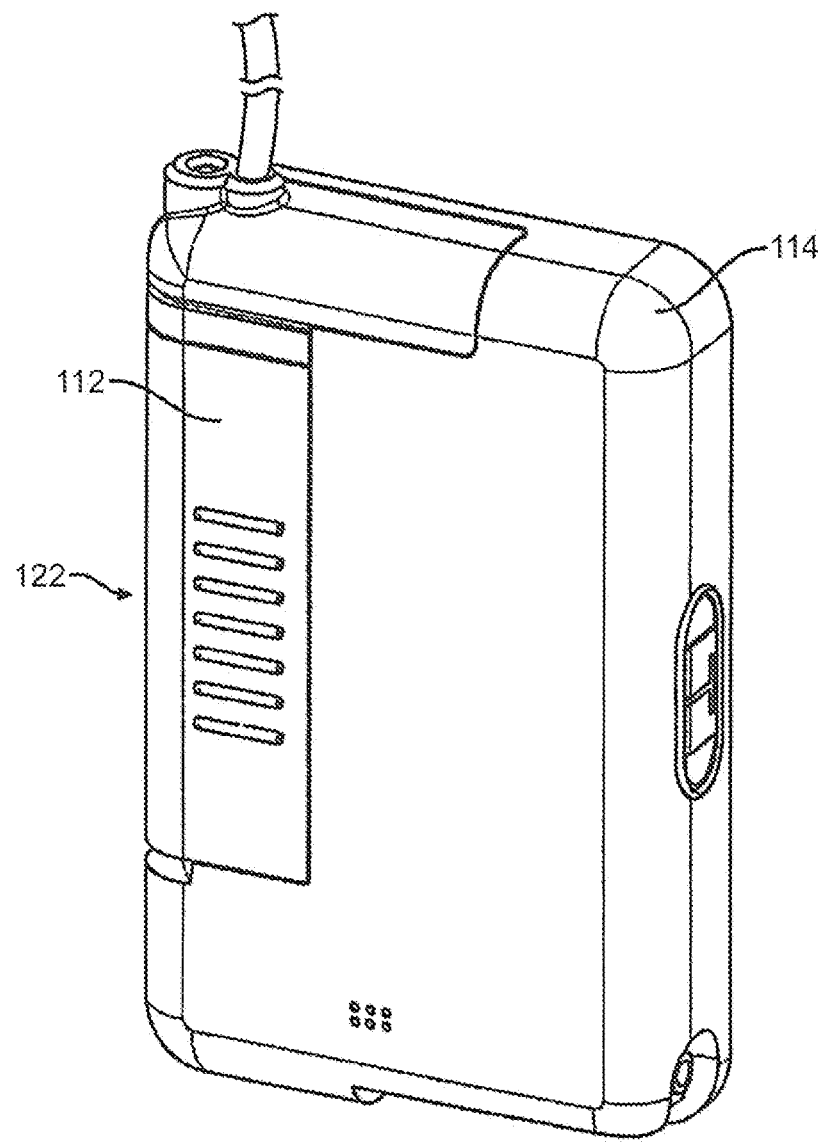
FIG. 1B is a rear perspective view of the infusion pump of FIG. 1A, including an attached infusion cartridge.

FIGS. 1A-1D depict an embodiment of a portable infusion pump system 110 including an infusion cartridge 112 and pump device 114. Infusion cartridge 112 can be a reversibly removable and interchangeable element that may be inserted into different pump devices. Referring to FIG. 1A, a front view of the pump device 114 is depicted and includes a user friendly user interface 116 on a front surface 118 of the pump device 114. The user interface 116 includes a touch sensitive screen 120 that may be configured to display a variety of screens used for displaying data, facilitating data entry by a patient, providing visual tutorials, as well as other interface features that may be useful to a patient operating the pump device 114. FIG. 1B is a rear view of the pump device 114 and illustrates the detachable installment of the infusion cartridge 112 in a slot 122 of the pump device 114 which is configured to accept the cartridge 112.

Figure 1C:
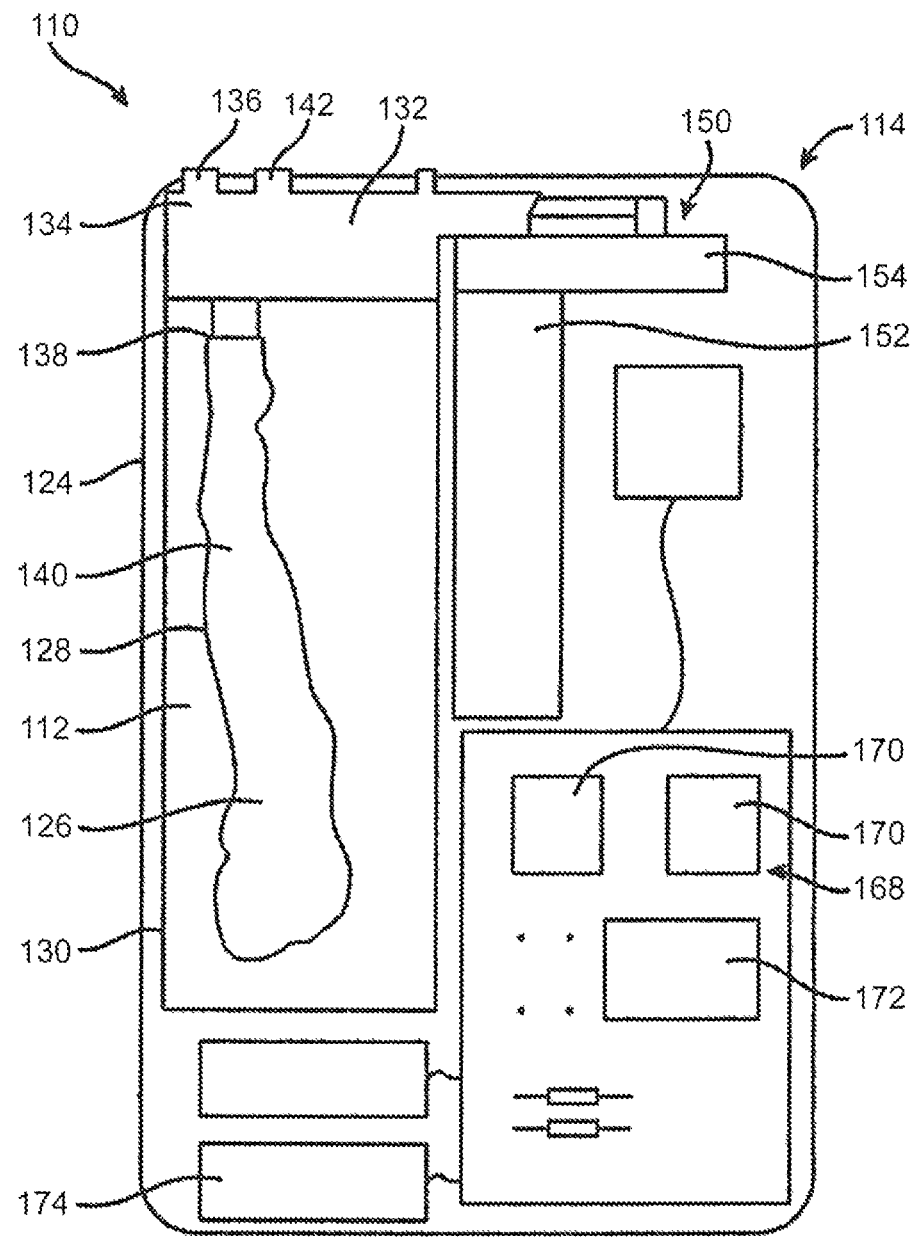
FIG. 1C is a rear schematic view of an interior of the infusion pump and cartridge embodiments of FIGS. 1A and 1B.

FIG. 1C is a schematic view of an open housing 124 of the pump device 114 depicting components that may be included in embodiments of the pump device 114. The cartridge 112 may include a fluid interface configured to receive a fluid such as collapsible reservoir 126. The collapsible reservoir 126 may be formed from a flexible material or membrane 128 that is disposed about an interior volume of the reservoir 126. The cartridge 112 also includes a substantially rigid container 130 sealed around the flexible material of the collapsible reservoir 126. A disposable delivery mechanism 132 is disposed within the disposable cartridge 112 and may have a fill port 134 with a re-sealable septum 136 sealed over the fill port 134, a reservoir inlet port 138 in fluid communication with an interior volume 140 of the collapsible reservoir 126, a fluid dispense port 142 in fluid communication with a bore 144 of the delivery mechanism 132, a vent inlet port 146 and a vent outlet port 148, both in fluid communication with the bore 144. The collapsible reservoir 126 may have a bag-like structure with flexible walls that can collapse and expand depending upon the amount of material in the volume of the reservoir. The interior volume of the reservoir may be in fluid isolation from the remaining interior volume of the rigid container 130.

The cartridge 112 may be releasably and operatively secured to a housing 124 of the pump device 114. The housing 124 may be configured to house a drive mechanism 150 including a motor 152 and gear box 154 disposed in the housing 124 and detachably coupled to a spool member 156 of the delivery mechanism 132. At least one pressure sensor 158 may be disposed in a volume 160 between an outside surface 162 of the flexible material or membrane 128 of the collapsible reservoir 126 and an inside surface 164 of the substantially rigid shell or case 130. The graphic user interface 116 may be operatively coupled to a controller 168, which may include at least one processor 170, a memory device 172 and connective circuitry or other data conduits that couple the data generating or data managing components of the device. A power storage cell in the form of a battery 174 that may be rechargeable may also be disposed within the housing 124. Data generating or managing components of the device may include the processor(s) 170, the memory device 172, sensors 158, including any pressure or temperature sensors, the GUI 166 and the like.

Figure 1D:
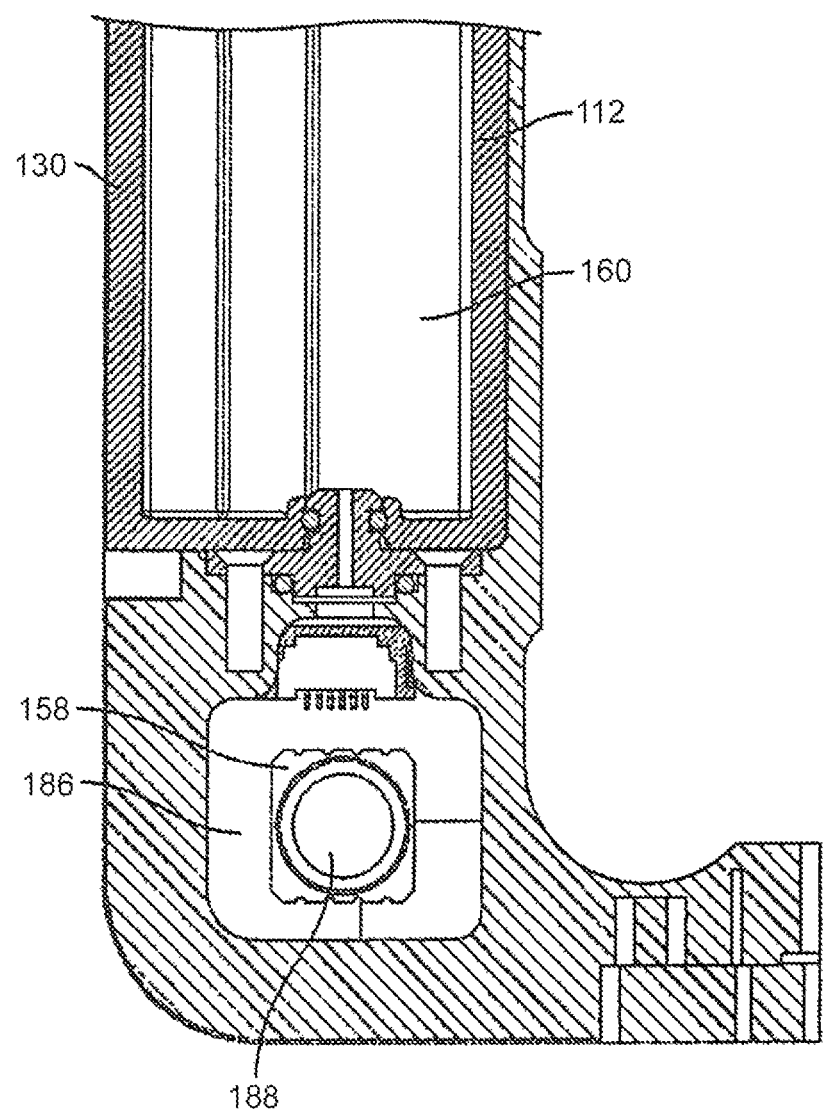
FIG. 1D is a partial sectional view of the infusion cartridge and pump device of FIGS. 1A and 1B.

The pressure inside the infusion cartridge 112, and particularly the vented volume 160 of the infusion cartridge 112, may be measured by a pressure sensor 158 disposed in the infusion cartridge 112 or in the pump device 114 in a volume, such as pocket 186 as shown in FIG. 1D.

Pocket 186 is an interior volume disposed within the pump device 114 and in fluid communication with an interior volume of the fluid cartridge 112. The pocket 186 is in sealed relationship with the interior volume 160 of the cartridge. As such, a pressure sensor 158 disposed within the volume of the pocket 186 will read the pressure of the volume 160 in the cartridge, but can remain with the pump device 114 after disposal of the disposable cartridge 112. This configuration lowers the cost of the cartridge while providing for pressure measurement within the cartridge 112. In some embodiments, data from the pressure sensor 158 may be used to provide a measurement of how much insulin or other medicament is being delivered by the first pump device 114. Alternatively, the pressure sensor 158 can be disposed within the cartridge directly in the vented volume 160.

The pump device 114 can also include a thermistor or other temperature sensor 188 including an optical or infrared sensor that measures the temperature of the insulin or other medicament within the reservoir 126 upon coupling the infusion cartridge 112 with the pump device 114. Taking the temperature of the air may be important in measuring how much insulin or other medicament is in the fluid reservoir. In some embodiments, the thermistor or other temperature sensor 188 is positioned in the pocket 186 such that it can measure the temperature of the air in the pocket 186 as shown in FIG. 1D. As noted above, the pocket 186 may also include a pressure sensor 158 coupled to the controller 168 for measuring pressure within the pocket 186 and volume 160. Because the air in the pocket 186 is in fluid communication with the residual air within the chamber 160, the temperature and pressure of the air in the infusion cartridge 112 surrounding the fluid reservoir 126 may be equal or approximately equal to the temperature and pressure of the air in contact with the temperature sensor 188 and pressure sensor 158. In turn, the temperature sensor 188 may provide a relatively accurate measurement of the temperature of the insulin or other medicament within the reservoir 126.

Referring to FIGS. 2-7, an embodiment of the delivery mechanism 132 is depicted in a fluid delivery cycle sequence wherein fluid from the interior volume of the reservoir 126 is drawn into the bore 220 of the delivery mechanism 132 and dispensed from the dispense outlet port 142.

Referring again to FIG. 2, a portion of the fluid reservoir cartridge 112 including a delivery mechanism 132 is shown in section as well as a portion of a drive mechanism 150 of an infusion pump. The disposable fluid cartridge 112 includes the delivery mechanism 132 which has a delivery mechanism body 236 and a bore 220 disposed in the delivery mechanism body 236. The bore 220, which may have a substantially round transverse cross section, includes a distal end 238, a proximal end 240 disposed towards the drive mechanism 150 of the infusion pump 114, an interior volume 242, a reservoir inlet port 138, a fluid dispense port 142, a vent inlet port 146 and a vent outlet port 148. The spool 156, which may also have a substantially round transverse cross section, is slidingly disposed within the bore 220 and forms a collapsible first volume 244 and a vent second volume 246 between the bore 220 and an outside surface 266 of the spool 156.

The collapsible first volume 244 of the delivery mechanism 132 may be positionable to overlap the reservoir inlet port 138 independent of an overlap of the fluid dispense port 142. The collapsible first volume 244 may be formed between a first seal 248 around the spool 156, a second seal 250 around the spool, an outer surface of the spool body between the first and second seal 250 and an interior surface 252 of the bore 220 between the first and second seal 248 and 250. The first and second seals 248 and 250 are axially moveable relative to each other so as to increase a volume of the collapsible volume 244 when the first and second seals 248 and 250 are moved away from each other and decrease the collapsible volume 244 when the seals 248 and 250 are moved closer together.

The second seal 250 is disposed on a main section 254 of the spool 156 of the delivery mechanism 132 and moves in conjunction with movement of the rest of the spool. A proximal end 196 of the spool 156 is coupled to a ball portion 194 of a drive shaft 190 of the drive mechanism 150 of the pump device 114. The drive mechanism 150 includes a rack and pinion 192 mechanism actuated by an electric motor 152 through a gear box 154. As such, the second seal 250 moves or translates axially in step with axial translation of the spool 156 and drive shaft 190. The first seal 248, however, is disposed on a distal section 258 of the spool 156 which is axially displaceable with respect to the main section 254 of the spool 156. The distal section of the spool 156 is coupled to the main section of the spool by an axial extension 260 that is mechanically captured by a cavity 261 in the main section 254 of the spool 156. This configuration allows a predetermined amount of relative free axial movement between the distal section 258 of the spool and the nominal main section 254 of the spool 156.

For some embodiments, a volume of a "bucket" of fluid dispensed by a complete and full dispense cycle of the spool 156 may be approximately equal to the cross section area of the bore 220 multiplied by the length of displacement of the captured axial extension of the spool 156 for the distal section 258. The complete bucket of fluid may also be dispensed in smaller sub-volumes in increments as small as a resolution of the drive mechanism 150 allows. For some embodiments, a dispense volume or bucket defined by the complete collapsible volume 244 of the delivery mechanism 132 may be divided into about 10 to about 100 sub-volumes to be delivered or dispensed. In some cases, the maximum axial displacement between the distal section and main section of the spool may be about 0.01 inch to about 0.04 inch, more specifically, about 0.018 inch, to about 0.022 inch.

Figure 2:
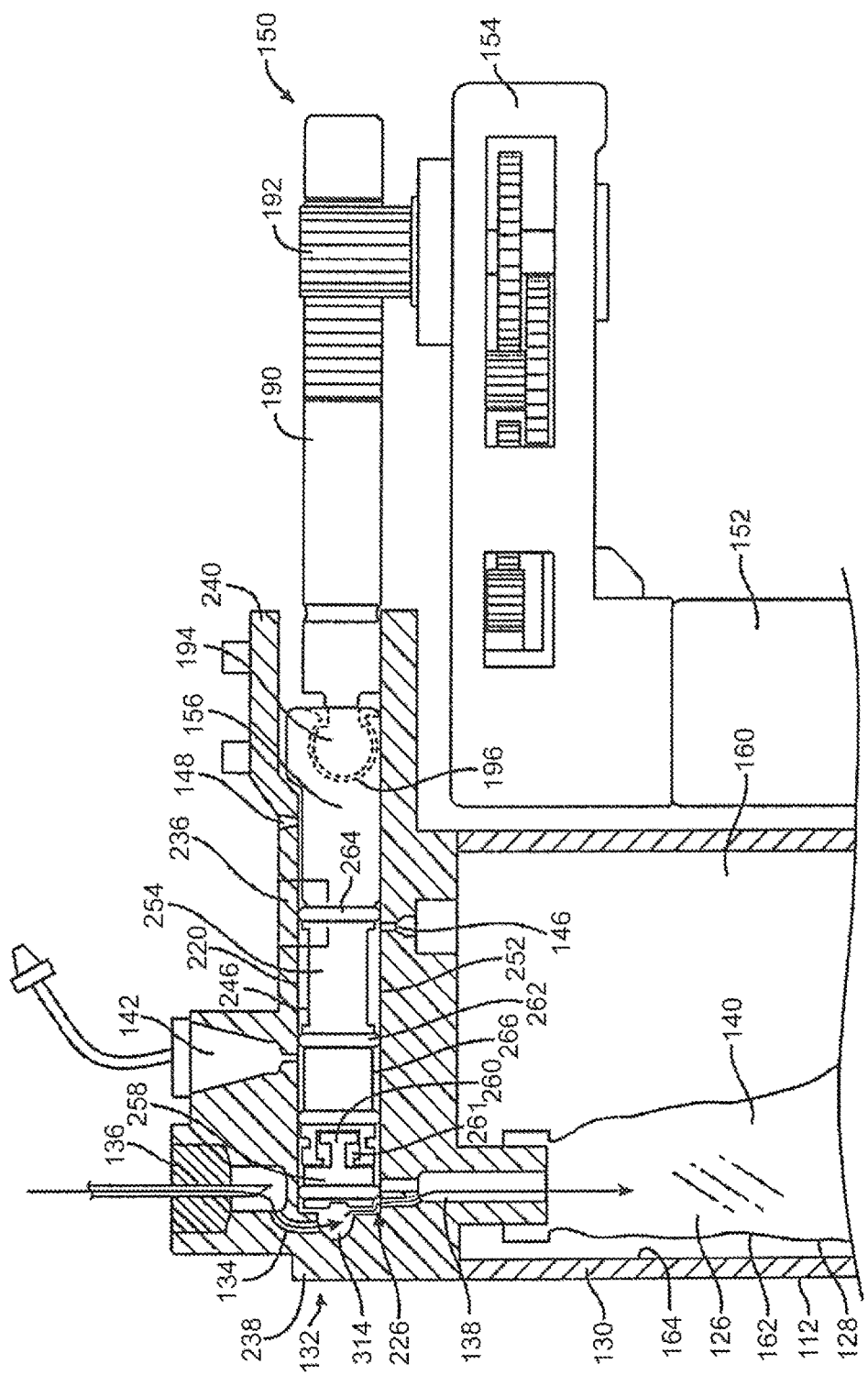
FIG. 2 is a partial sectional view of a delivery mechanism of an infusion pump with the spool of the delivery mechanism positioned at a distal hard stop for filling of the expandable reservoir according to an embodiment of the present invention.
Figure 3:
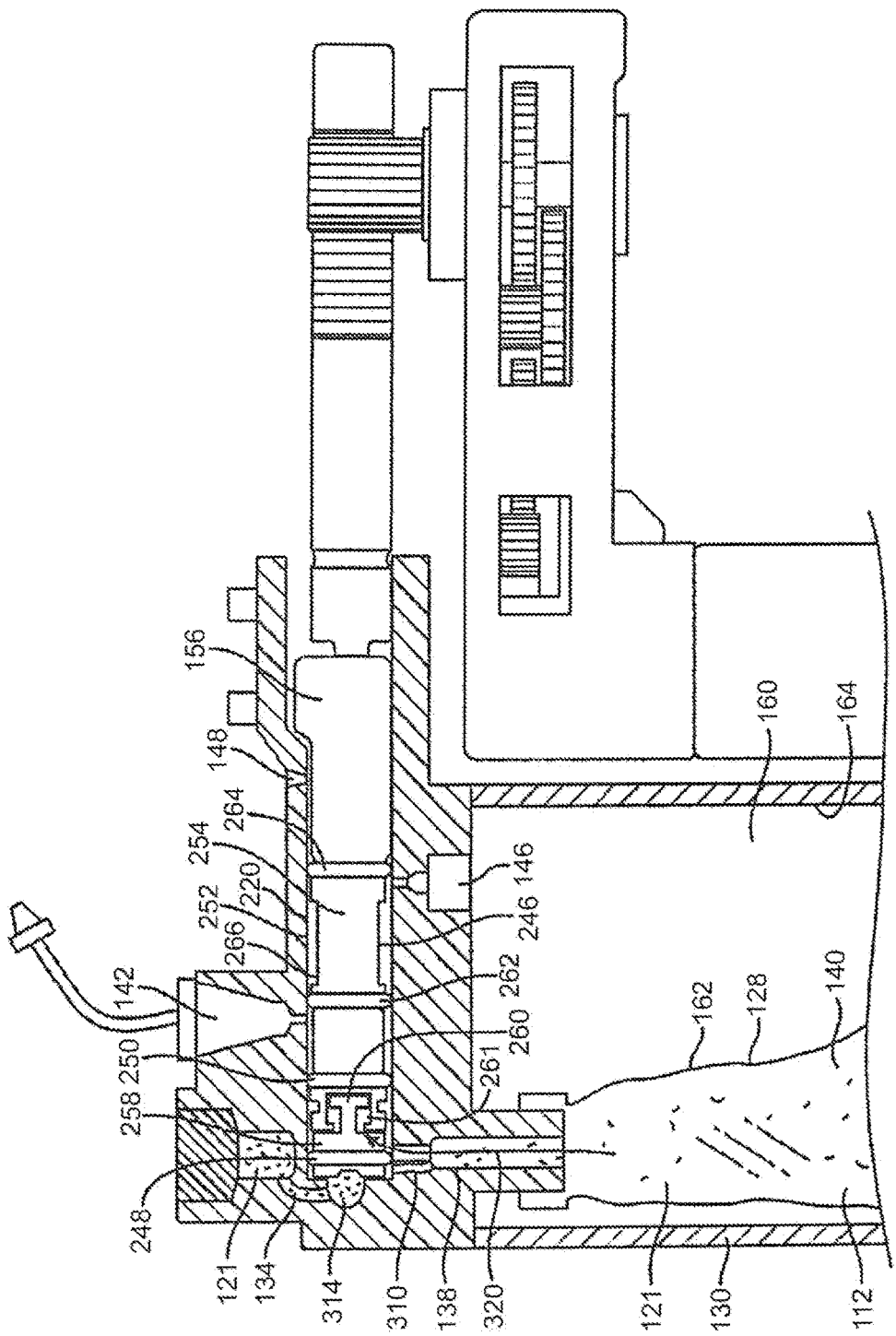
FIG. 3 is similar to FIG. 2, but with the spool of the delivery mechanism positioned for filling of a collapsible volume of the spool.

In use, once the reservoir cartridge 112 of the infusion pump system 110 has been installed or otherwise snapped into place in the slot 122 of the pump device 114, the interior volume 140 of the collapsible reservoir 126 may then be filled with a desired fluid 121 for dispensing. In order to fill the reservoir 126, the spool 156 may be translated by the drive mechanism 150 to a hard stop position 226 as shown in FIG. 2. In the hard stop position 226 the first seal 248 is disposed proximally of a relief port 310, the relief port 310 being disposed in fluid communication between a distal end 238 of the bore 220 and the reservoir volume 140. In the hard stop position, the first seal 248 is also disposed distally of the reservoir inlet port 138. In the hard stop position, a distal end 316 of the spool 156 is contacting the distal end 238 of the bore 220 or a shoulder portion 312 of the distal end 238 of the bore 220 to prevent any further distal displacement of the spool 156.

A reservoir fill port 134 is disposed on a top portion of the bore 220 substantially opposite the bore 220 of the reservoir inlet port 138. With the spool 156 and seals 248, 250, 262 and 264 thereof so positioned, a patient may then obtain an amount of a desired fluid to be dispensed. In some cases, if the desired fluid to be dispensed is insulin or other suitable medicament, the patient 127 typically stores the insulin in a refrigerated glass container. The insulin is then accessed with a hypodermic needle 222 of a syringe device and drawn into an interior volume of the syringe (not shown). The tip of the hypodermic needle 222 of the syringe may then be pushed through a septum membrane 136 that seals the reservoir fill port 134 as shown and fluid is manually dispensed from the interior volume of the syringe, through the hypodermic needle 222, through a bubble trap volume 314 in the bore 220 of the delivery mechanism 132 and into the interior volume 140 of the collapsible reservoir 126 of the cartridge 112 as shown by the arrow 318 in FIG. 2.

As discussed above with regard to other embodiments of the delivery mechanism 132, the vented volume 160 of the cartridge 112 disposed between an outside surface 162 of the flexible membrane 128 of the collapsible reservoir 126 and an inside surface 164 of the rigid shell 130 may include or be in operative communication with a pressure sensor 158. The pressure sensor 158 may be used to monitor the pressure within the vented volume 160 during the filling of the collapsible reservoir 126. The controller 168 of the pump system 114 may be programmed with information regarding the fixed volume of the rigid shell 130 of the cartridge 112 and configured to calculate the volume of fluid loaded into the collapsible reservoir 126 based on the pressure rise within the rigid shell 130 upon filling of the collapsible reservoir 126. The data regarding the volume of fluid loaded into the collapsible reservoir 126 may be stored and used to calculate and display data later in the use cycle such as fluid remaining in the collapsible reservoir 126 and the like.

Once the collapsible reservoir 126 contains a desired amount of a fluid 121 to be dispensed, a dispense cycle may be initiated by driving the spool 156 with the drive mechanism 150 based on commands from a controller 168 of the pump device to a position with the collapsible first volume 244 in communication with the reservoir inlet port 138. The hard stop position depicted in FIG. 2 is such a position. If the spool 156 has been driven to this hard stop position 226 in a distal direction from previous proximal position, the friction generated between the first seal 248 of the spool 156 and the inside surface 252 of the bore 220 will have collapsed the collapsible volume 244 of the delivery mechanism 132 with the first seal 248 and second seal 250 in a least axially separated state. In this state, the collapsible volume 244 has a minimum volume. Such a state of the delivery mechanism 132 is shown in FIG. 2. Once in this pre-fill position, the spool 156 may then be driven so as to axially separate the first and second seals 248 and 250 (and the main section 254 of the spool 156 and distal section 258 of the spool 156) of the collapsible first volume 244 and draw fluid into the first volume 244 through the reservoir inlet port 138 from the reservoir 126 as shown by the arrow 320 in FIG. 3. As the fluid 121 is drawn into the collapsible volume 244, the pressure within the vented volume 160 decreases. As previously discussed, this drop in pressure may be used in accordance with the ideal gas law to determine the amount of material taken from the collapsible reservoir 126. An unexpected reading based on the magnitude of the translation of the main section 254 of the spool 156 may also be used to detect a failure of a portion of the delivery mechanism 132 in some cases.

Figure 4:
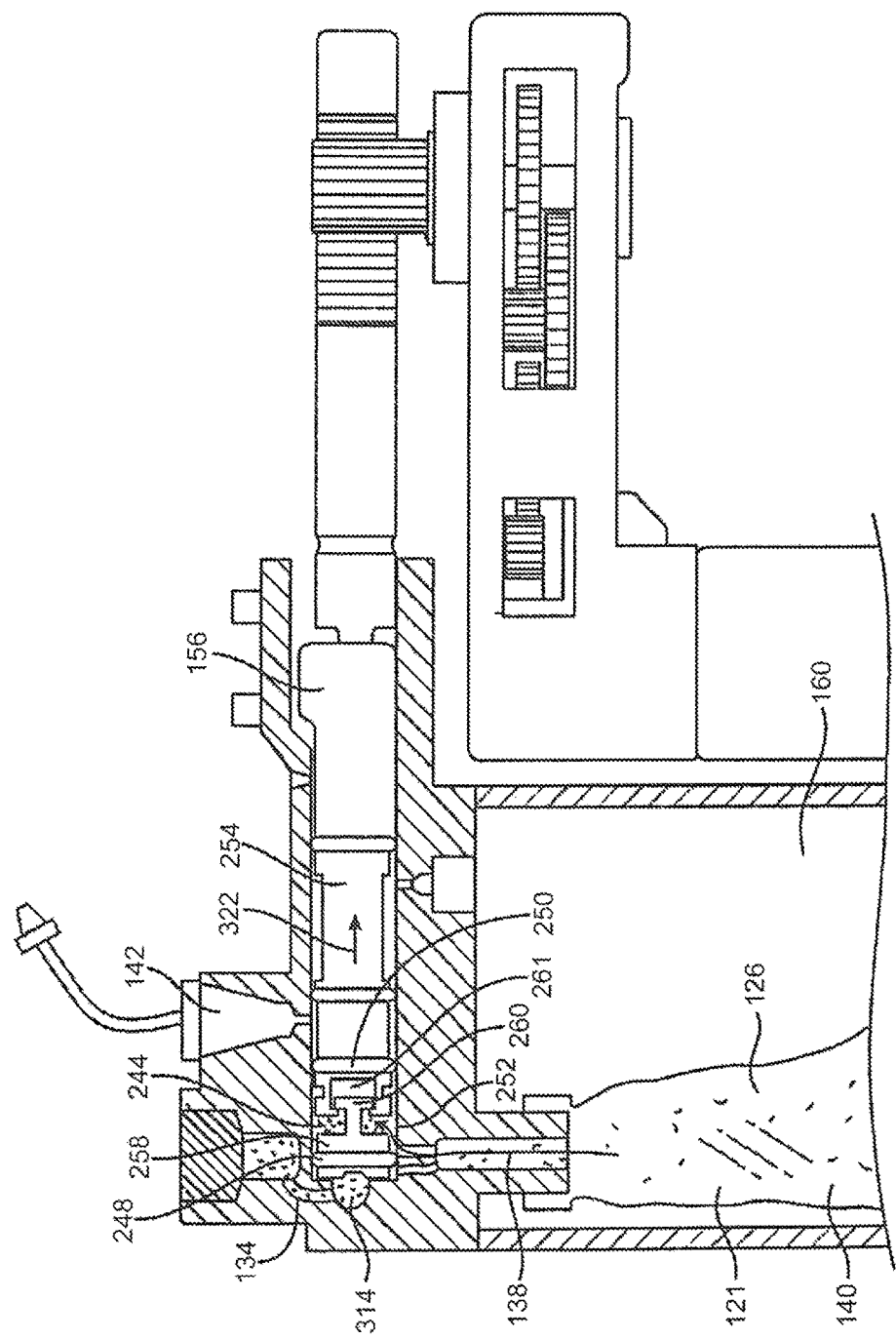
FIG. 4 is similar to FIG. 2, but with the spool of the delivery mechanism positioned after filling of the collapsible volume of the spool.
Figure 5:
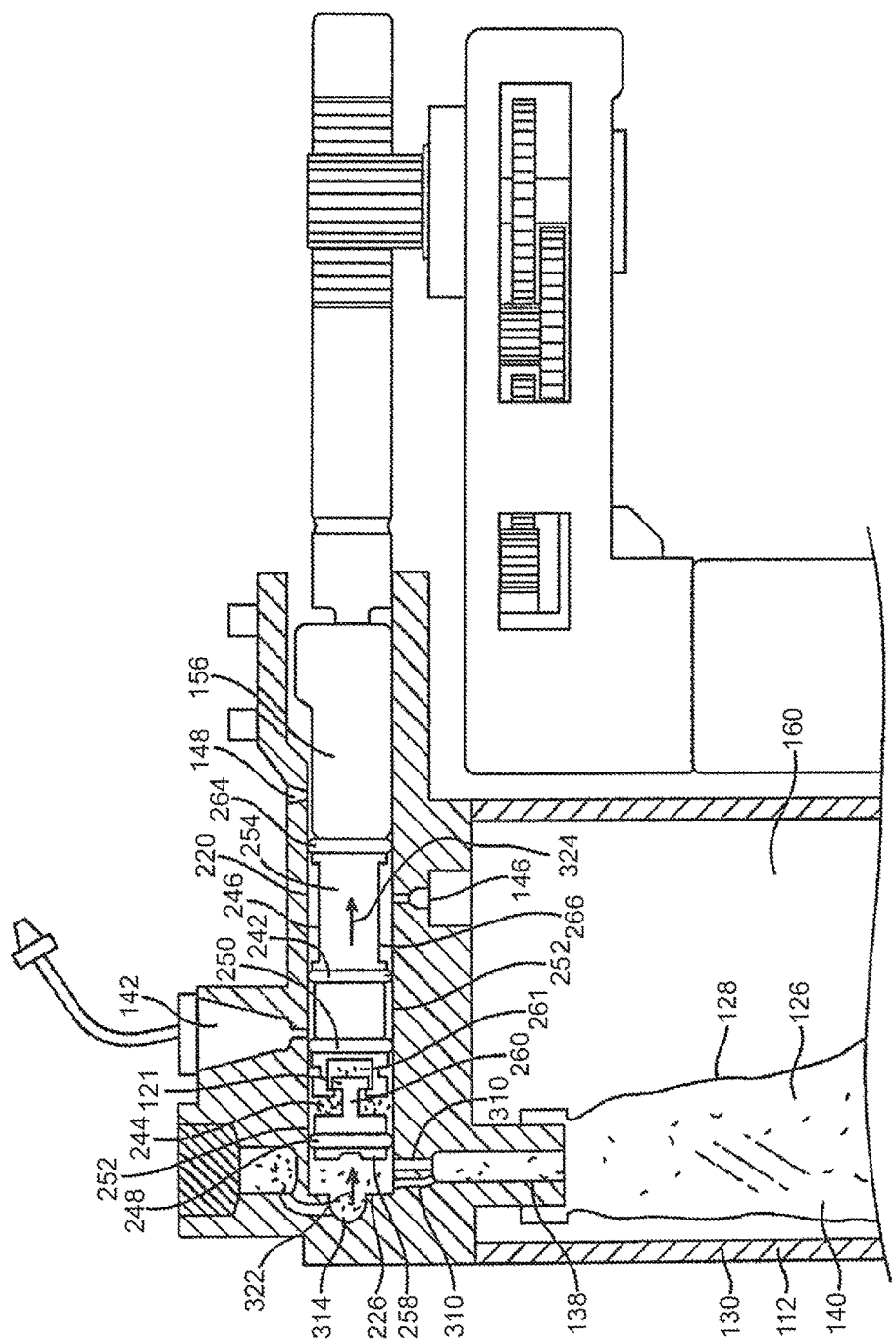
FIG. 5 is similar to FIG. 2, but with the collapsible volume of the device full of fluid being displaced proximally towards the dispense port of the device.

The collapsible volume 244 of the delivery mechanism 132 may be completely filled by proximally retracting the main section 254 and second seal 250 of the spool 156 relative to the first seal 248 and distal section 258 of the spool 156 as shown by arrow 322 on spool 156 in FIG. 4. Once filled, the spool 156 may then be driven in a proximal direction as shown in FIG. 5 wherein there are two seals 248 and 250 disposed in the bore 220 between the reservoir inlet port 138 and relief port 310 and the dispense port 142. As shown by arrow 323 and arrow 324 in FIG. 5, both the main section 254 and distal section 258 of the spool 156 are proximally retracted together. The captured axial extension of the distal section 258 by the main section 254 pulls the distal section along without axial displacement between the main section 254 and distal section 258 of the spool 156. The dispense port may be in fluid communication with a subcutaneous portion of a patient's body. The delivery mechanism 132 always includes at least one seal 248 or 250 disposed in the bore 220 between the reservoir volume 140 and material 121 disposed therein and the dispense port 142 in order to prevent a free flow condition wherein the material 121 in the reservoir 126 is in uninterrupted communication with the patient's body.

Figure 6:
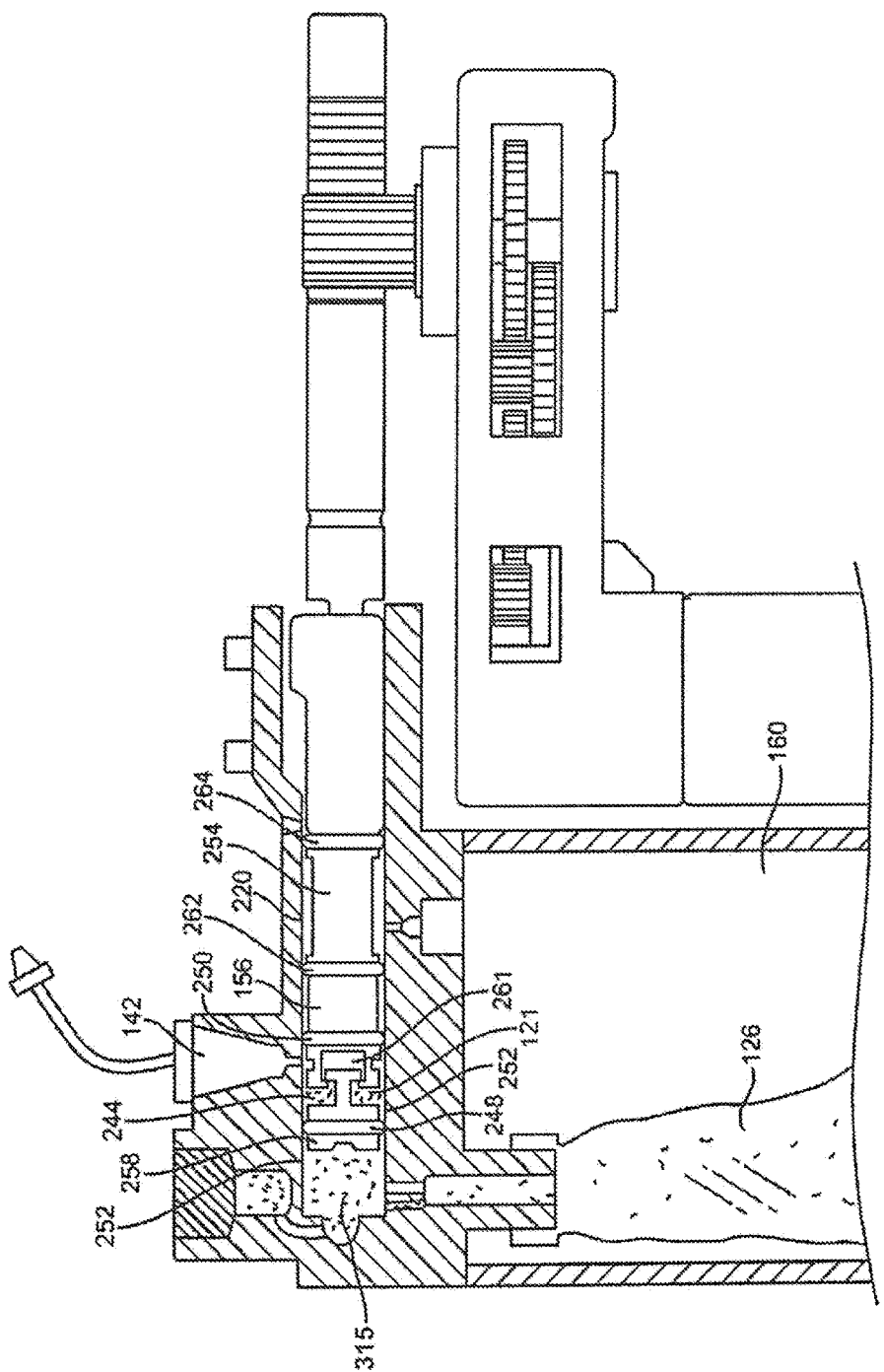
FIG. 6 is similar to FIG. 2, but with the spool of the delivery mechanism positioned prior to delivery of fluid into the dispense port from the collapsible volume of the spool.
Figure 7:
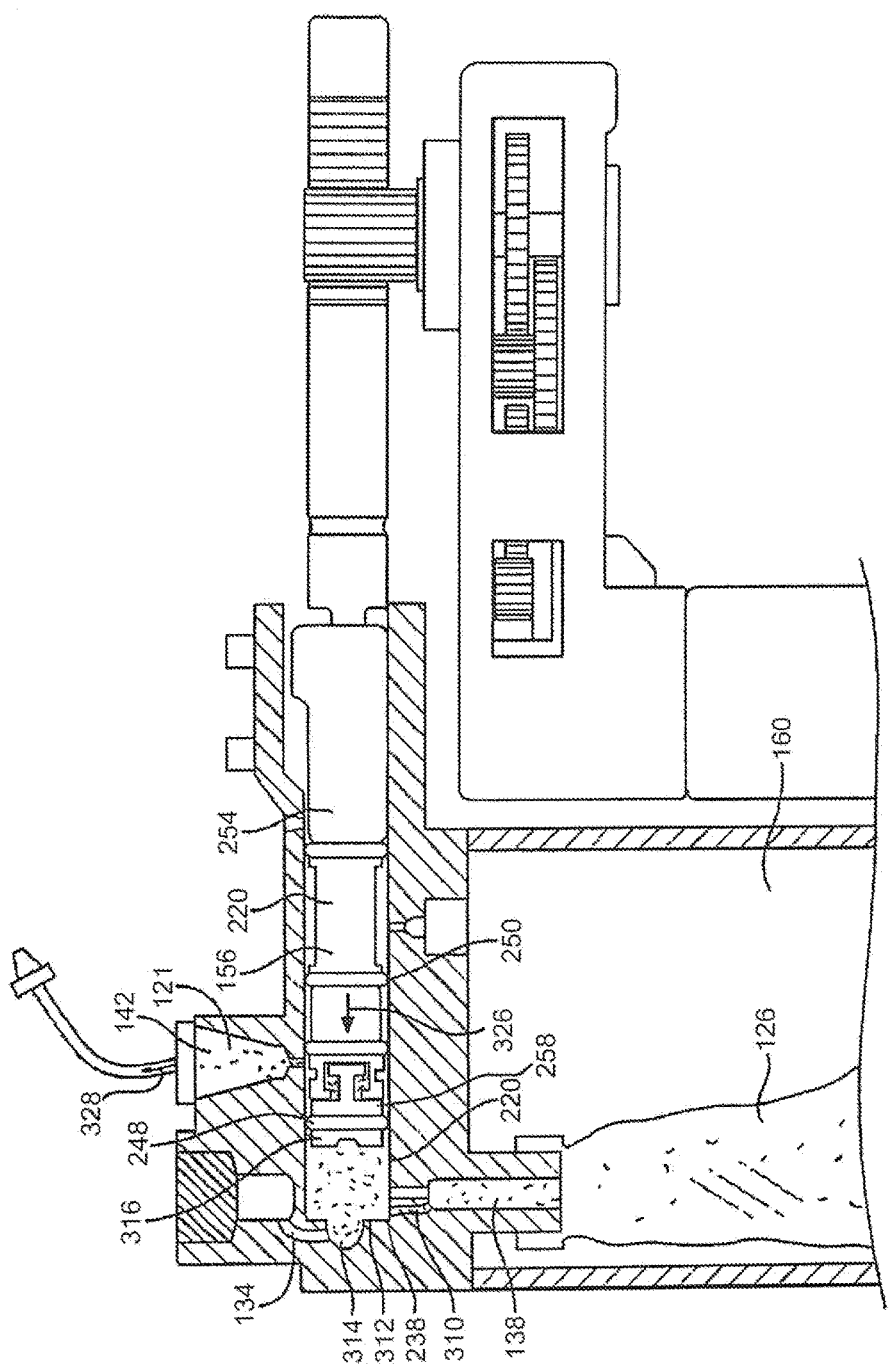
FIG. 7 is similar to FIG. 2, but with the spool of the delivery mechanism positioned after delivery of fluid from the collapsible volume of the spool into the dispense port.
Figure 8:
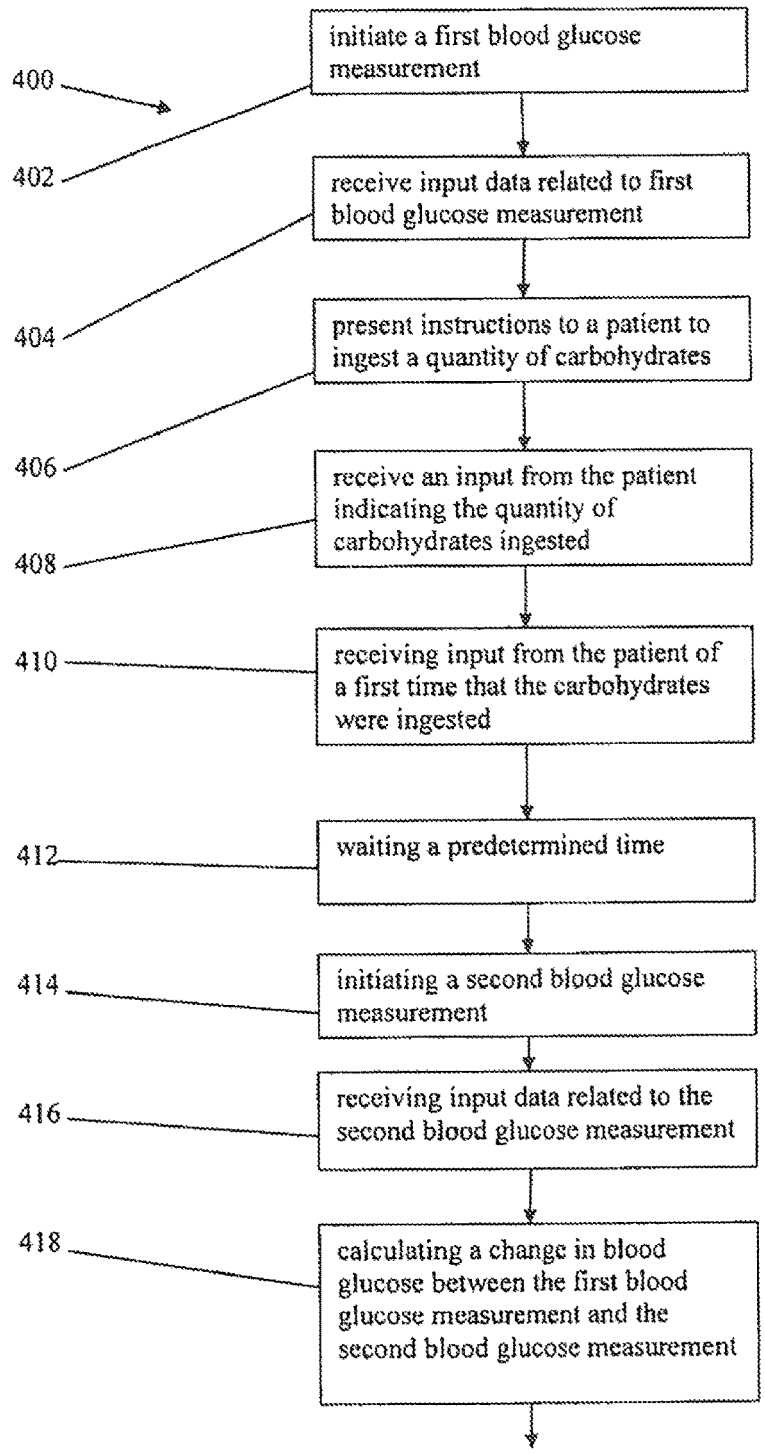
FIG. 8 is a flow chart illustrating a method of operation according to an embodiment of the invention and also representing a method that may be programmed into and implemented by a computer controller in an infusion pump.
Figure 8:
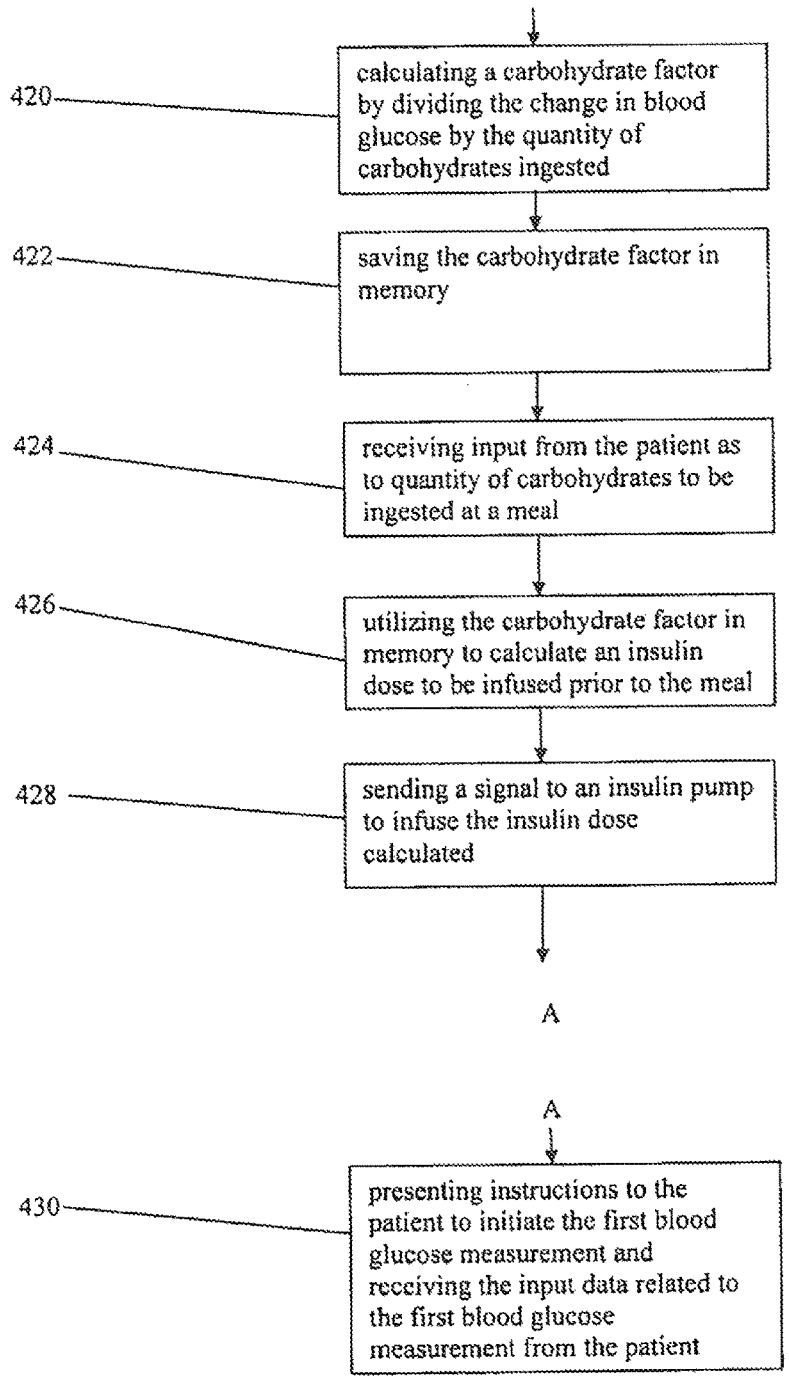
Figure 8:
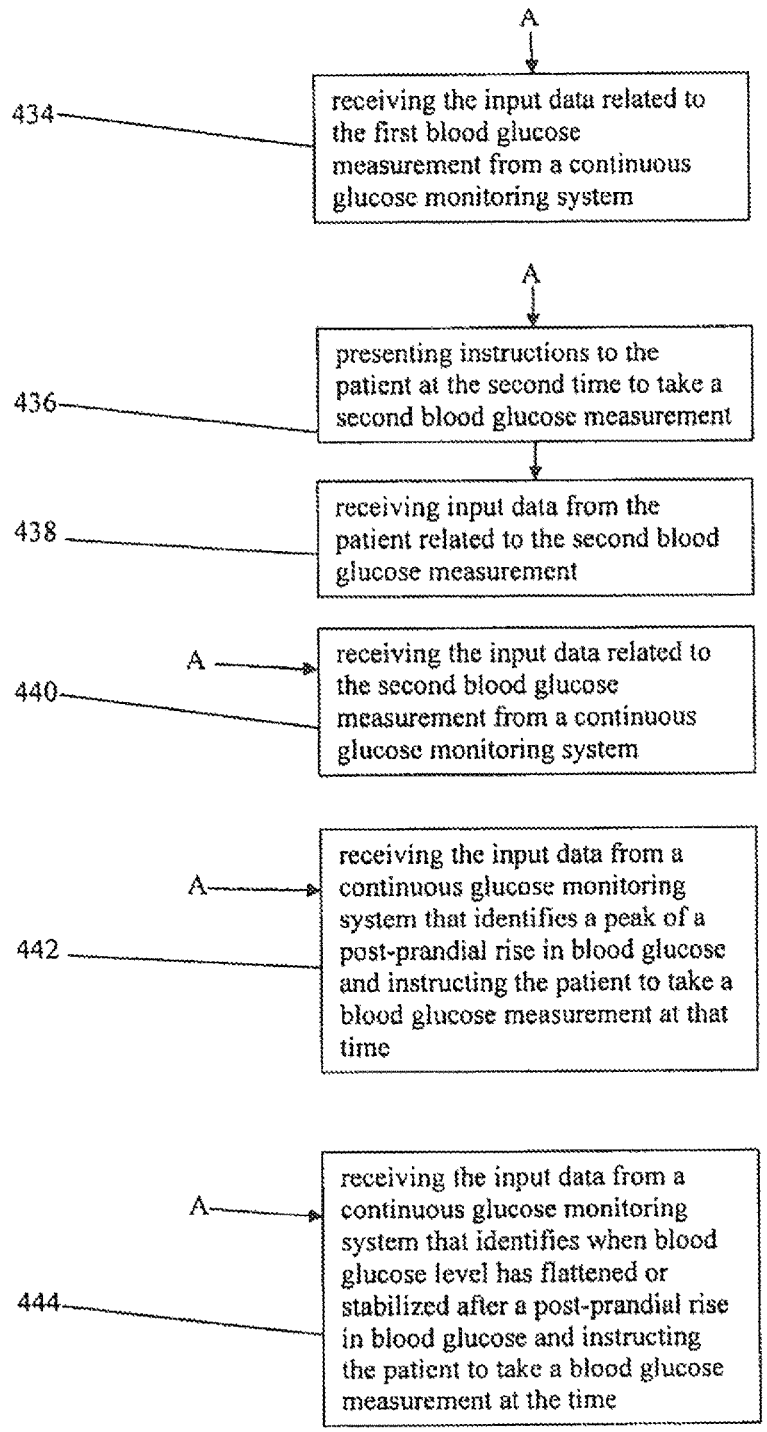
Figure 9:
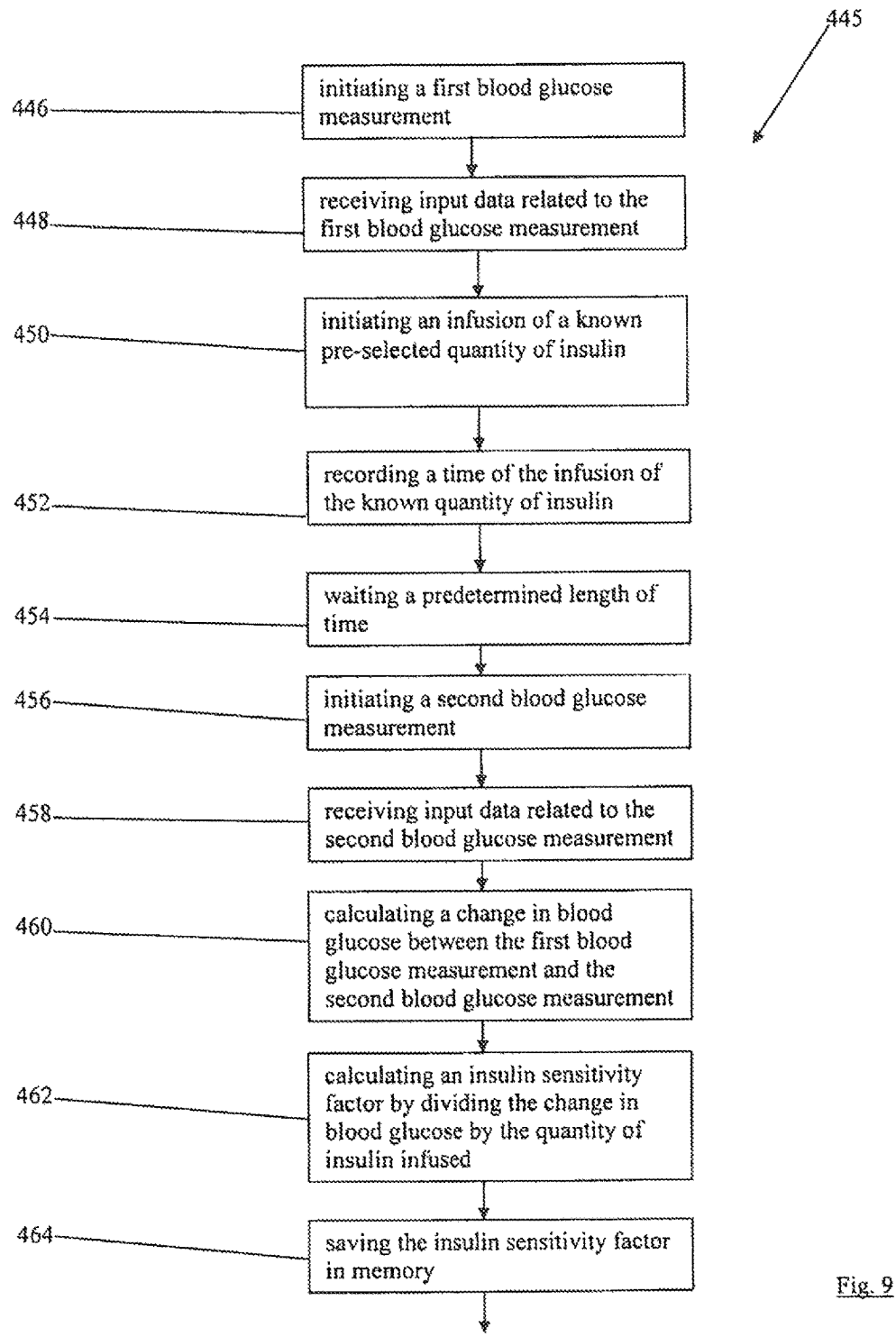
FIG. 9 is another flow chart illustrating a method of operation according to an embodiment of the invention and also representing a method that may be programmed into and implemented by a computer controller in an infusion pump.
Figure 9:
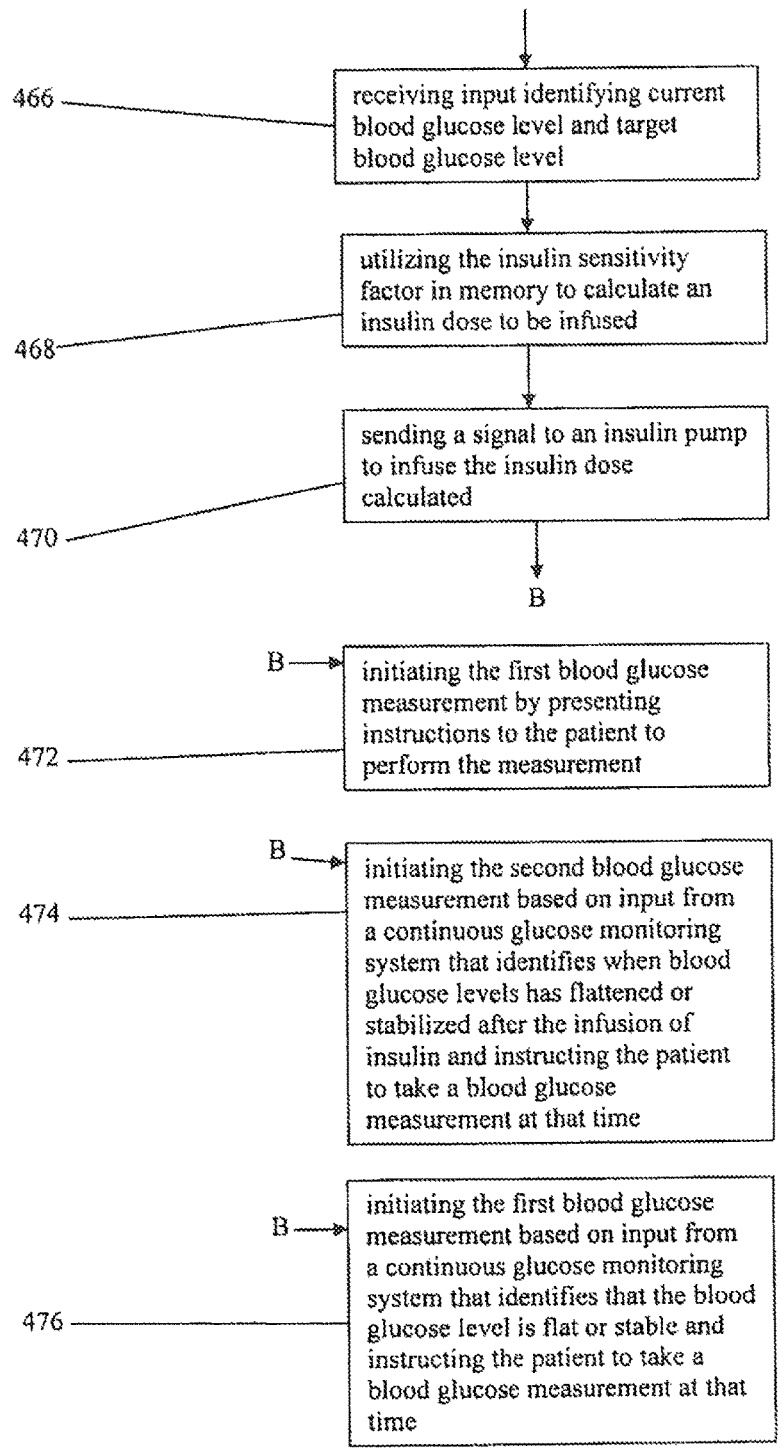
Figure 9:
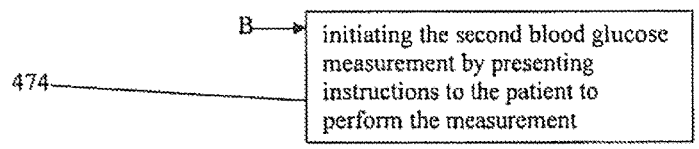

Once filled, the spool 156 and filled collapsible volume 244 may be proximally displaced with the drive mechanism 150 to a position with the collapsible first volume 244 in communication with the fluid dispense port 142 of the bore 220 as shown in FIG. 6. Once the spool 156 is positioned as depicted in FIG. 6, the main section of the spool 156 may then be axially driven in a distal direction by the drive mechanism 150 with the distal section 258 of the spool remaining stationary or substantially stationary. This axial distal movement of the main section 254 as indicated by arrow 326 on the spool 156 depicted in FIG. 7, serves to at least partially collapse the collapsible first volume 244. Collapsing the first volume 244 of the delivery mechanism 132 dispenses fluid from the collapsible first volume 244 through the fluid dispense port 142 as shown by the arrow 328 in FIG. 7. Once all fluid from the collapsible first volume 244 is dispensed in this manner, additional cycles as described above can be completed to provide additional insulin to the patient. Further details on the operation and configuration of such an infusion pump can be found in U.S. Pat. No. 8,287,495 which is hereby incorporated by reference herein in its entirety.

According to an embodiment of the invention, the method 400 includes initiating a first blood glucose measurement 402, receiving input data related to first blood glucose measurement 404, presenting instructions to a patient to ingest a quantity of carbohydrates 406, receiving an input from the patient indicating the quantity of carbohydrates ingested 408, receiving input from the patient of a first time that the carbohydrates were ingested 410, waiting a predetermined period of time 412, initiating a second blood glucose measurement 414, receiving input data related to the second blood glucose measurement 416, calculating a change in blood glucose between the first blood glucose measurement and the second blood glucose measurement 418, calculating a carbohydrate factor by dividing the change in blood glucose by the quantity of carbohydrates ingested 420, saving the carbohydrate factor in memory 422, receiving input from the patient as to quantity of carbohydrates to be ingested at a meal 424, utilizing the carbohydrate factor in memory to calculate an insulin dose to be infused prior to the meal 426 and sending a signal to an infusion device controller to infuse the insulin dose 428.

Figure 12:
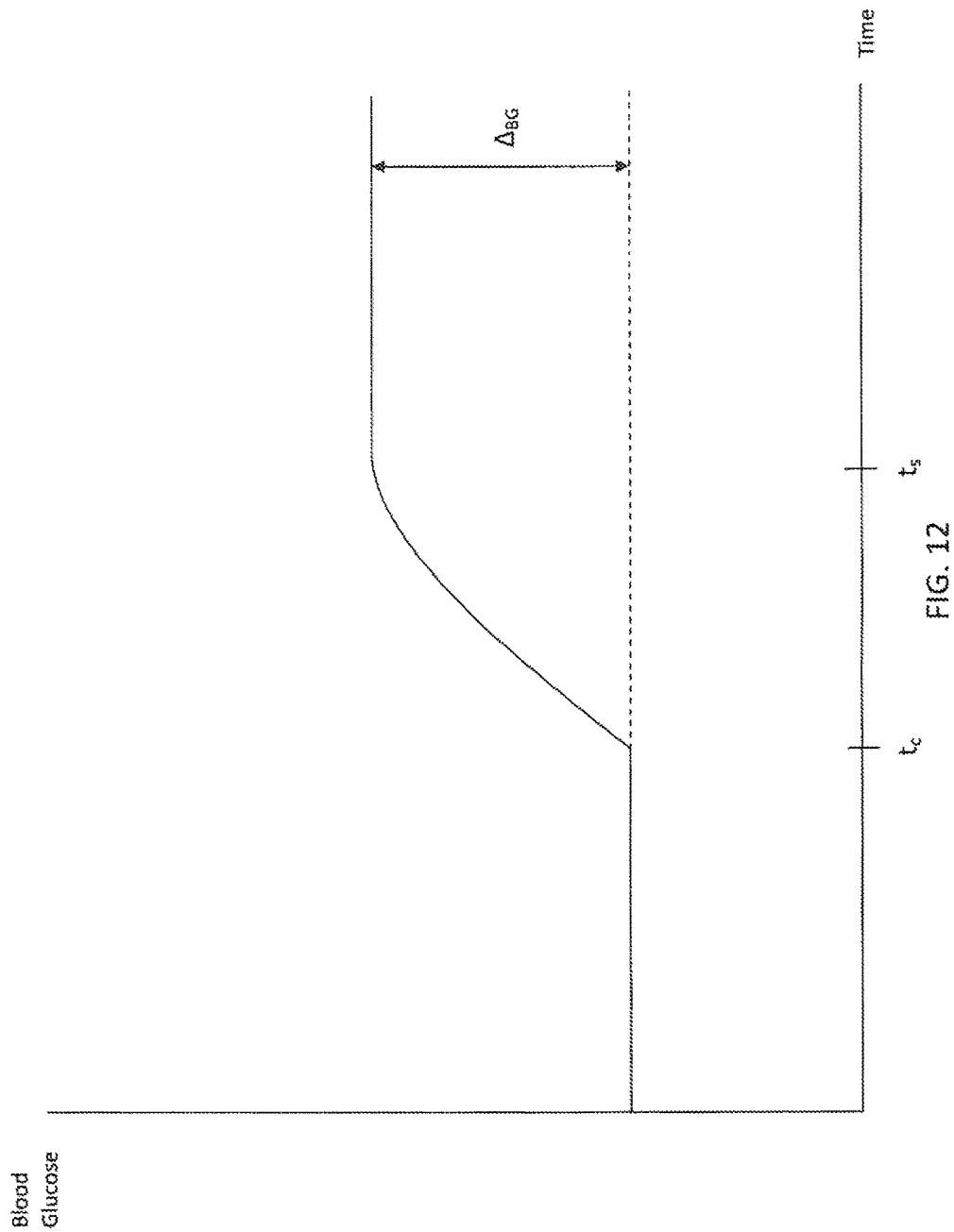

FIG. 12 depicts a graph of blood glucose versus time that relates to calculation of a carbohydrate factor as described herein. Up until time $t_c$, the patient's blood glucose is stable at a first level. At time $t_c$, the carbohydrates ingested by the user begin raising the user's blood glucose level until it is done increasing and/or levels off at a second, higher level at time $t_s$. The change in blood glucose between the time levels, $\Delta_{BG}$, can be used along with the known amount of carbohydrates consumed to determine the individual's carbohydrate factor.

Alternately, the taking of blood glucose level measurements can be based on waiting a minimum amount of time and alerting the patient to take a second blood glucose level measurement at a time when data from the CGM indicates that the rate of change of blood glucose level has decreased to below a preselected threshold.

According to another embodiment of the invention, the invention may further include presenting instructions to the patient to initiate the first blood glucose measurement and receiving the input data related to the first blood glucose measurement from the patient 430. The instructions may be presented visually or verbally (such as by voice emulation software). For example, instructions may be presented via interface 116.

According to another embodiment of the invention, the invention may include receiving the input data related to the first blood glucose measurement from a continuous glucose monitoring system 434 such as those described above and in documents incorporated by reference herein.

According to another embodiment of the invention, the invention may include presenting instructions to the patient at the second time to take a second blood glucose measurement 436 and receiving input data from the patient related to the second blood glucose measurement 438.

According to another embodiment of the invention, the method may include receiving the input data related to the second blood glucose measurement from a continuous glucose monitoring system 440.

According to another embodiment of the invention, the invention may include receiving the input data from a continuous glucose monitoring system that identifies a peak of a postprandial rise in blood glucose and instructing the patient to take a blood glucose measurement at that time 442.

According to another embodiment of the invention, the method may include receiving the input data from a continuous glucose monitoring system that identifies when blood glucose level has flattened or stabilized after a postprandial rise in blood glucose and instructing the patient to take a blood glucose measurement at that time 444.

According to another embodiment of the invention, the invention includes a computer implemented method of determining an insulin sensitivity factor utilizing an insulin pump 445. The computer may include an onboard controller or processor incorporated into an ambulatory infusion device as well as a remote device that is in communication with the onboard controller or processor.

The method may include initiating a first blood glucose measurement 446, receiving input data related to the first blood glucose measurement 448, initiating an infusion of a known pre-selected quantity of insulin 450, recording a time of the infusion of the known quantity of insulin 452, waiting a predetermined length of time 454, initiating a second blood glucose measurement 456, receiving input data related to the second blood glucose measurement 458, calculating a change in blood glucose between the first blood glucose measurement and the second blood glucose measurement 460, calculating an insulin sensitivity factor by dividing the change in blood glucose by the quantity of insulin infused 462, saving the insulin sensitivity factor in memory 464, receiving input identifying current blood glucose level and target blood glucose level 466, utilizing the insulin sensitivity factor in memory to calculate an insulin dose to be infused 468 and sending a signal to an insulin pump to infuse the insulin dose calculated 470.

Figure 11:
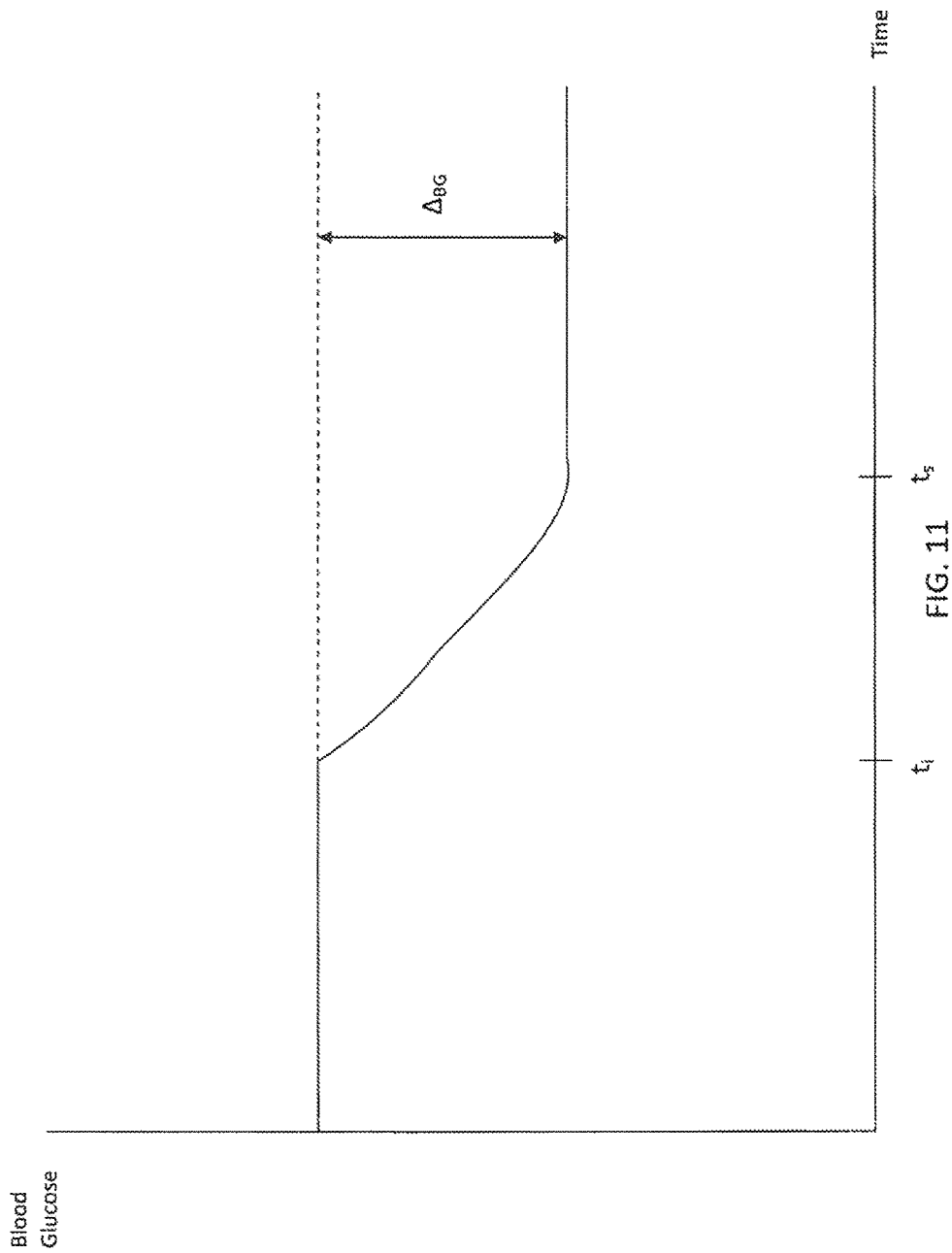
FIGS. 11-13 depict various graphs of blood glucose level versus time.

FIG. 11 depicts a graph of blood glucose versus time that relates to calculation of an insulin sensitivity factor as described herein. The user takes a known quantity of insulin. Up until time $t_i$, the patient's blood glucose is stable at a first level. At time $t_i$, the insulin begins dropping the user's blood glucose level until it is done decreasing and/or levels off at a second, lower level at time $t_s$. The change in blood glucose between the time levels, $\Delta_{BG}$, can be used along with the known amount of insulin ingested to determine the individual's insulin sensitivity factor.

An embodiment of the invention may further include initiating the first blood glucose measurement by presenting instructions, for example, to the patient to perform the measurement 472.

According to another embodiment of the invention, the invention may include initiating the second blood glucose measurement based on input from a continuous glucose monitoring system that identifies when blood glucose levels have flattened or stabilized after the infusion of insulin and instructing, for example, the patient to take a blood glucose measurement at that time 474.

Alternately, the taking of blood glucose level measurements can be based on waiting a minimum amount of time and alerting the patient to take a second blood glucose level measurement at a time when data from the CGM indicates that the rate of change of blood glucose level has decreased to below a preselected threshold. According to another embodiment of the invention, the invention may include initiating the first blood glucose measurement based on input from a continuous glucose monitoring system that identifies that the blood glucose level is flat or stable and instructing, for example, the patient to take a blood glucose measurement at that time 476.

According to another embodiment of the invention, the invention may include initiating the second blood glucose measurement by presenting instructions, for example, to the patient to perform the measurement 478.

According to another embodiment of the invention, the invention includes an ambulatory infusion device including a controller programmed with an algorithm to cause the insulin pump to execute a method as discussed above.

According to another embodiment, the invention includes determining the insulin action time. After a bolus of insulin is infused, blood glucose level will decrease. This reduction is observable with CGM. Accordingly this method is well suited to be performed along with the insulin sensitivity factor determination discussed herein. After a bolus of insulin is infused the time for a selected reduction in blood glucose level to be achieved is recorded. This determines the insulin action time.

Figure 10:
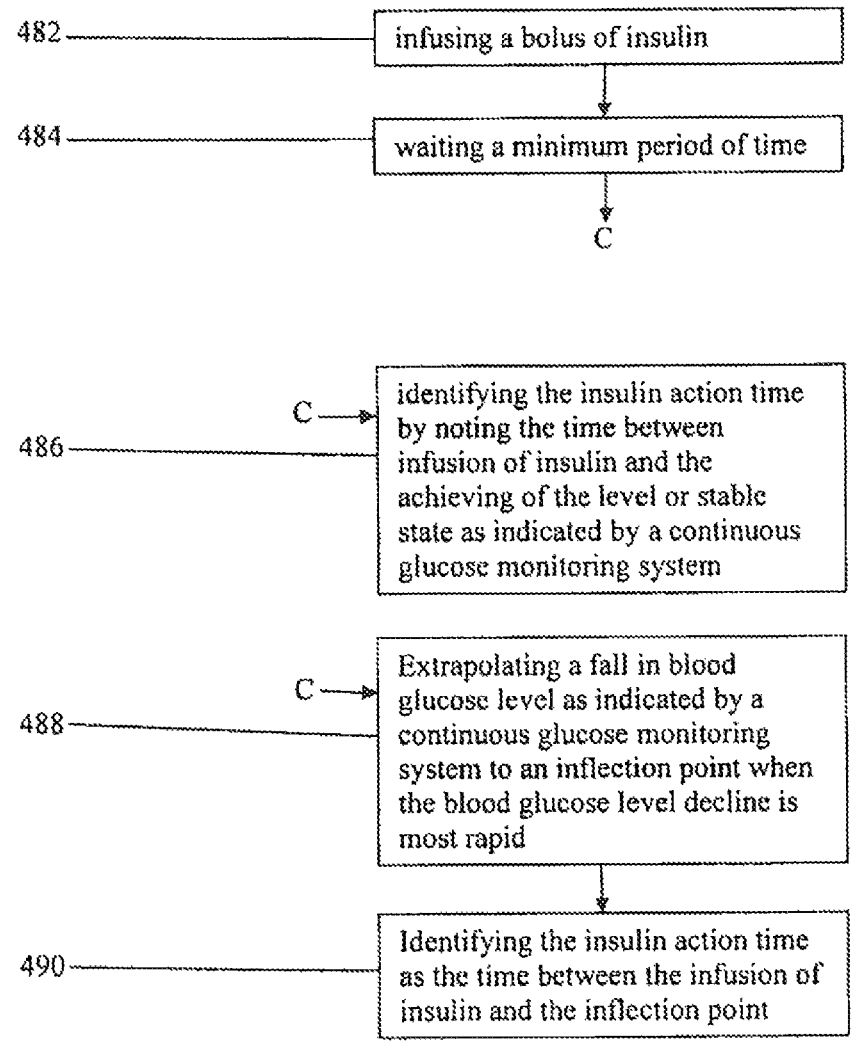
FIG. 10 is another flow chart illustrating a method of determining insulin action time.

Referring to FIG. 10, a method of determining insulin action time, according to an embodiment of the invention includes infusing a bolus of insulin 482; waiting a minimum period of time 484; receiving an input from the CGM that the blood glucose level has reached a level or stable state; identifying the insulin action time by noting the time between infusion of insulin and the achieving of the level or stable state 486. Alternately, the fall in blood glucose level according to the CGM can be extrapolated to an inflection point when the blood glucose level decline is most rapid 488. The time between infusion of the insulin and the inflection can be taken as the insulin action time 490.

Figure 13:
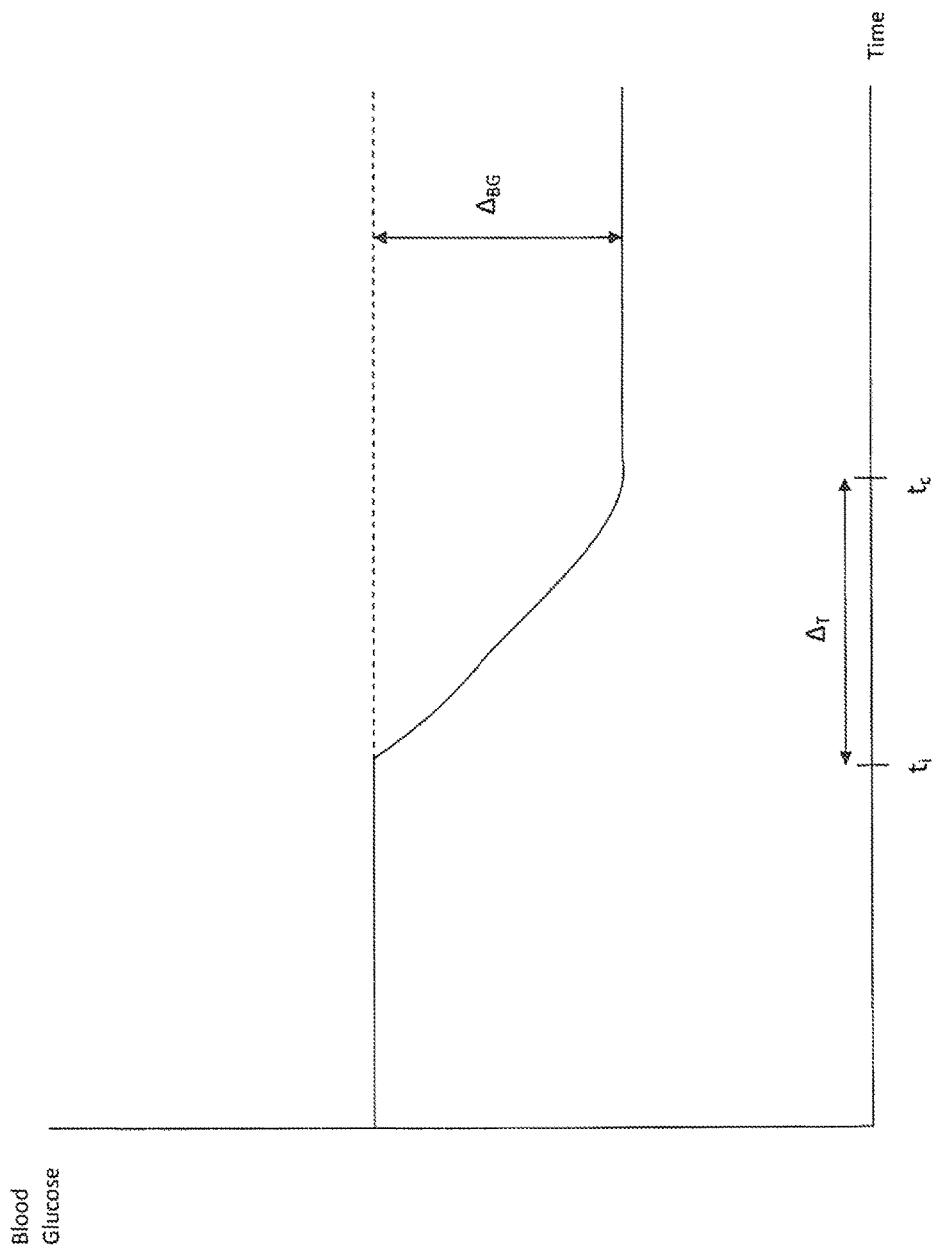

FIG. 13 depicts a graph of blood glucose versus time that relates to calculation of an insulin sensitivity factor as described herein. Up until time $t_i$, the patient's blood glucose is stable at a first level. At time $t_i$, the user takes a known quantity of insulin. In response to the insulin, the user's blood glucose level drops until it is done decreasing and/or levels off at a second, lower level at time $t_s$. The time that the blood glucose level takes to go from the first level to the second level between $t_i$ and $t_s$, $\Delta_t$, can be used to determine the insulin action time.

The present invention may be embodied in other specific forms without departing from the spirit of the essential attributes thereof; therefore, the illustrated embodiments should be considered in all respects as illustrative and not restrictive, reference being made to the appended claims rather than to the foregoing description to indicate the scope of the invention.

The invention claimed is:

1. An ambulatory infusion pump for infusing insulin into a living being, the pump having a controller, the controller being programmed with an algorithm that executes the following:

receiving input data related to a first blood glucose measurement;

presenting instructions to a user to ingest a quantity of carbohydrates;

receiving an input from the user indicating the quantity of carbohydrates ingested;

receiving input data related to a second blood glucose measurement at a time after the input indicating the quantity of carbohydrates ingested;

calculating a change in blood glucose between the first blood glucose measurement and the second blood glucose measurement;

calculating a carbohydrate factor by dividing the change in blood glucose by the quantity of carbohydrates ingested;

saving the carbohydrate factor in memory;

receiving input from the user as to a quantity of carbohydrates to be ingested at a subsequent meal after saving the carbohydrate factor into memory;

utilizing the carbohydrate factor in memory to calculate an insulin dose to be infused prior to the meal; and causing the pump to infuse the insulin dose, wherein the time of the second blood glucose measurement is determined based on an identification of a peak of a postprandial rise in blood glucose based on input from a continuous glucose monitoring system.

2. The automated ambulatory infusion pump as claimed in claim 1, wherein the algorithm further executes: receiving the input data related to the first blood glucose measurement or the second blood glucose measurement from the continuous glucose monitoring system.

3. The automated ambulatory infusion pump as claimed in claim 1, wherein the algorithm further executes: presenting instructions to the user to initiate the first blood glucose measurement or presenting instructions to the user to initiate the second blood glucose measurement.

4. An ambulatory infusion pump for infusing insulin into a living being, the pump having a controller, the controller being programmed with an algorithm that executes the following:

receiving input data related to a first blood glucose measurement;

presenting instructions to a user to ingest a quantity of carbohydrates;

receiving an input from the user indicating the quantity of carbohydrates ingested;

receiving input data related to a second blood glucose measurement at a time after the input indicating the quantity of carbohydrates ingested;

calculating a change in blood glucose between the first blood glucose measurement and the second blood glucose measurement;

calculating a carbohydrate factor by dividing the change in blood glucose by the quantity of carbohydrates ingested;

saving the carbohydrate factor in memory;

receiving input from the user as to a quantity of carbohydrates to be ingested at a subsequent meal after saving the carbohydrate factor into memory;

utilizing the carbohydrate factor in memory to calculate an insulin dose to be infused prior to the meal; and causing the pump to infuse the insulin dose, wherein the time of the second blood glucose measurement is determined based on an identification of when blood glucose level has stabilized after a postprandial rise in blood glucose based on input from a continuous glucose monitoring system.

5. The automated ambulatory infusion pump as claimed in claim 4, wherein the algorithm further executes: receiving the input data related to the first blood glucose measurement or the second blood glucose measurement from the continuous glucose monitoring system.

6. The automated ambulatory infusion pump as claimed in claim 4, wherein the algorithm further executes: presenting instructions to the user to initiate the first blood glucose measurement or presenting instructions to the user to initiate the second blood glucose measurement.

* * * * *